US009873915B2

(12) United States Patent
Mirza et al.

(10) Patent No.: US 9,873,915 B2
(45) Date of Patent: Jan. 23, 2018

(54) GRADING, STAGING AND PROGNOSING CANCER USING OSTEOPONTIN-C

(75) Inventors: Mana Mirza, Jazan (SA); Elizabeth Shaughnessy, Cincinnati, OH (US); Georg F. Weber, Cincinnati, OH (US); John K. Hurley, Tucson, AZ (US); Kristie A. Vanpatten, Oro Valley, AZ (US); Gary Pestano, Oro Valley, AZ (US)

(73) Assignees: Ventana Medical Systems, Inc., Tucson, AZ (US); University of Cincinnati, Cincinnati, OH (US)

( * ) Notice: Subject to any disclaimer, the term of this patent is extended or adjusted under 35 U.S.C. 154(b) by 319 days.

(21) Appl. No.: 12/682,310

(22) PCT Filed: Oct. 16, 2008

(86) PCT No.: PCT/US2008/080162
§ 371 (c)(1),
(2), (4) Date: Apr. 9, 2010

(87) PCT Pub. No.: WO2009/052286
PCT Pub. Date: Apr. 23, 2009

(65) Prior Publication Data
US 2010/0209928 A1 Aug. 19, 2010

Related U.S. Application Data

(60) Provisional application No. 60/980,379, filed on Oct. 16, 2007.

(51) Int. Cl.
*C12Q 1/68* (2006.01)
*A61K 47/68* (2017.01)

(52) U.S. Cl.
CPC ........ *C12Q 1/6886* (2013.01); *A61K 47/6855* (2017.08); *C12Q 2600/106* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| 7,056,674 | B2 | 6/2006 | Baker et al. | |
|---|---|---|---|---|
| 7,081,340 | B2 | 7/2006 | Baker et al. | |
| 2003/0124128 | A1* | 7/2003 | Lillie et al. | 424/155.1 |
| 2004/0142865 | A1 | 7/2004 | Weber | |

FOREIGN PATENT DOCUMENTS

WO  WO 2007/149948 A2  12/2007

OTHER PUBLICATIONS

Takafuji (Oncogene, 2007, 26, p. 6361-6371).*
Carey (Clin Cancer Res, 2007, 13:2329-2334).*
Ahr et al, "Molecular classification of breast cancer patients by gene expression profiling," Journal of Pathology, 2001, vol. 195, p. 312-320.
Andre et al, "Molecular classification of breast cancer: implications for selection of adjuvant chemotherapy," Nature Clinical Practice Oncology, Nov. 2006, vol. 3, No. 11, p. 621-632.
Chan and Sell Tumor Markers: In: Burtis CA Ashwood ER, editors. Tietz fundamental of clinical chemistry, 5th ed. Philadelphia: WB Saunders; 2001, p. 390-413.
Clark GM, In: Harris JLM, Morrow M., Hellman S., editors. Prognostic and Predictive Factors, Philadelphia: Lippincott-Raven; 1996, p. 461-485.
Coppola et al, "Correlation of Osteopontin Protein Expression and Pathological Stage across a Wide Variety of Tumor Histologies," Clinical Cancer Research, Jan. 1, 2004, vol. 10, p. 184-190.
Crawford et al, "Distinct Roles of Osteopontin in Host Defense Activity and Tumor Survival during Squamous Cell Carcinoma Progression in Vivo," Cancer Research, Nov. 15, 1998, vol. 58, p. 5206-5215.
Cronin et al, "Measurement of Gene Expression in Archival Paraffin-Embedded Tissues," American Journal of Pathology, Jan. 2004, vol. 164, No. 1, p. 35-42.
Database Product Catalogue (Online) May 31, 2007, retrieved from Gallus Immunotech, Database, Accession No. AhOPNc, 2 pages.
Desruisseau et al, "Clinical Relevance of Amphiregulin and VEGF in Primary Breast Cancers," Int. J. Cancer, 2004, vol. 111, p. 733-740.
Elston et al, "Pathological prognostic factors in breast cancer. I. The value of histological grade in breast cancer: experience from a large study with long-term follow up," Histopathology, 1991, vol. 19, p. 403-410.
Forootan et al, "Prognostic significance of osteopontin expression in human prostate cancer," Int. J. Cancer, 2006, vol. 118, p. 2225-2261.
Hayes et al, "Assessing the clinical impact of prognostic factors: When is "statistically significant" clinically useful?," Breast Cancer Research and Treatment, 1998, vol. 52, p. 305-319.
He et al, "An osteopontin splice variant induces anchorage independence in human breast cancer cells," Oncogene, 2006, vol. 25, p. 2192-2202.
Henry et al, "Uses and Abuses of Tumor Markers in the Diagnosis, Monitoring, and Treatment of Primary and Metastatic Breast Cancer," The Oncologist, 2006, vol. 11, p. 541-552.

(Continued)

Primary Examiner — Sarae L Bausch
(74) Attorney, Agent, or Firm — Ventana Medical Systems, Inc.

(57) ABSTRACT

The present disclosure provides methods and kits that can be used to determine the grade or stage of a breast or other cancer, such as a ductal carcinoma in situ (DCIS). By determining the grade, stage, or aggressiveness of a cancer, appropriate therapeutic regiments can be selected and administered to the patient with the cancer. The method includes detecting osteopontin-c (OPN-c), wherein the presence of high amounts of OPN-c in the cancer sample indicates that the subject has a more aggressive form of cancer (e.g., grade 3).

10 Claims, 8 Drawing Sheets

(56) References Cited

OTHER PUBLICATIONS

Kasugai et al, "Differential regulation of the 55 and 44 kDa forms of secreted phosphoprotein 1 (SPP-1, osteopontin) in normal and transformed rat bone cells by osteotropic hormones, growth factors and a tumor promoter," Bone and Mineral, 1991, vol. 13, p. 235-250.
Kleer et al, "EZH2 is a marker of aggressive breast cancer and promotes neoplastic transformation of breast epithelial cells," PNAS, Sep. 30, 2003, vol. 100, No. 20, p. 11606-11611.
Kon et al, "Antibodies to Different Peptides in Osteopontin Reveal Complexities in the Various Secreted Forms," Journal of Cellular Biochemistry, 2000, vol. 77, p. 487-498.
Mirza et al, "Osteopontin-c is a selective marker of breast cancer," Int. J. Cancer, 2008, vol. 122, p. 889-897.
Oncotype DX Development (Online), retrieved from www.genomichealth.com, print out, Oct. 10, 2007, 2 pages.
Paik et al, "A Multigene Assay to Predict Recurrence of Tamoxifen-Treated, Node-Negative Breast Cancer," The New England Journal of Medicine, Dec. 30, 2004, vol. 351, No. 27, p. 2817-2826.
Pan et al, "Overexpression of Osteopontin Is Associated with Intrahepatic Metastasis, Early Recurrence, and Poorer Prognosis of Surgically Resected Hepatocellular Carcinoma," Cancer, 2003, vol. 98, p. 119-127.
Patani et al, Int. J. Cancer, 2008, vol. 122, p. 2646.
Rakha et al, "Prognostic Markers in Triple-Negative Breast Cancer," Cancer, 2007, vol. 109, p. 25-32.
Rudland et al, "Prognostic Significance of the Metastasis-associated Protein Osteopontin in Human Breast Cancer," Cancer Research, Jun. 15, 2002, vol. 62, p. 3417-3427.
Singhal et al, "Elevated Plasma Osteopontin in Metastatic Breast Cancer Associated with Increased Tumor Burden and Decreased Survival," Clinical Cancer Research, Apr. 1997, vol. 3, p. 605-611.
Sotiriou et al, "Gene Expression Profiling in Breast Cancer: Understanding the Molecular Basis of Histologic Grade to Improve Prognosis," Journal of the National Cancer Institute, Feb. 15, 2006, vol. 98, No. 4, p. 262-272.
Takafuji et al, "An osteopontin fragment is essential for tumor cell invasion in hepatocellular carcinoma," Oncogene, 2007, vol. 26, p. 6361-6371.
van't Veer et al, "Gene expression profiling predicts clinical outcome of breast cancer," Nature, Jan. 31, 2002, vol. 415, p. 530-536.
van de Vijver et al, "A Gene-Expression Signature as a Predictor of Survival in Breast Cancer," The New England Journal of Medicine, Dec. 19, 2002, vol. 347, No. 25, p. 1999-2009.
Wang et al, "Gene Expression profiles to predict distant metastasis of lymph-node-negative primary breast cancer," Lancet, Feb. 19, 2005, vol. 365, p. 671-679.
Weber et al, "Stress response genes: the genes that make cancer metastasize," J. Mol. Med., 2000, vol. 78, p. 404-408.
Yu et al, "A Molecular Signature of the Nottingham Prognostic Index in Breast Cancer," Cancer Research, May 1, 2004, vol. 64, p. 2962-2968.
Yu et al, "Pathway analysis of gene signatures predicting metastasis of node-negative primary breast cancer," BMC Cancer, 2007, vol. 7, No. 182, 14 pages.
Zhang et al, "Growth Factor Signaling Induces Metastasis Genes in Transformed Cells: Molecular Connection between Akt Kinase and Osteopontin in Breast Cancer," Molecular and Cellular Biology, Sep. 2003, vol. 23, No. 18, p. 6507-6519.
Zhou et al, "Osteopontin Expression Correlates with Melanoma Invasion," J. Invest. Dermatol., 2005, vol. 124, p. 1044-1052.
International Preliminary Report on Patentability for PCT Application No. PCT/US2008/080162, dated Apr. 20, 2010, 9 pages.
International Search Report for PCT Application No. PCT/US2008/080162, dated Feb. 13, 2009, 6 pages.
OMIM Public Database, Entry No. 133430, Estrogen Receptorl, ESR 1, pp. 1-44.
OMIM Public Database, Entry No. 607311, Progesterone Receptor, PGR, pp. 1-11.
Genbank Public Database, Accession No. BC128574, Strausberg et al, Dec. 5, 2006, pp. 1-5.
Genbank Public Database, Accession No. P03372, Green et al, Mar. 23, 2010, pp. 1-23.
Genbank Public Database, Accession No. NM_001005862, Takahashi et al, Apr. 11, 2010, pp. 1-12.
Genbank Public Database, Accession No. NM_004448, Takahashi et al, Apr. 11, 2010, pp. 1-11.
Genbank Public Database, Accession No. NP_001005862, Takahashi et al, Apr. 11, 2010, pp. 1-9.
Genbank Public Database, Accession No. NP_004439, Takahashi et al, Apr. 11, 2010, pp. 1-9.
Genbank Public Database, Accession No. BAA05951, Saitoh et al, Feb. 8, 2003, pp. 1-3.
Genbank Public Database, Accession No. D28761, Saitoh et al, Feb. 8, 2003, pp. 1-3.
Genbank Public Database, Accession No. AF016381, Kieback et al, Jan. 5, 1999, pp. 1-4.
Genbank Public Database, Accession No. AAD01587, Kieback et al, Jan. 5, 1999, pp. 1-3.
Hammond et al., ASCO/CAP Guideline Recommendations for Immunohistochemical Testing of Estrogen and Progesterone Receptors in Breast Cancer, J. Clinical Oncology, vol. 28, No. 16, p. 2784-95 (Apr. 19, 2010).
Wolff et al., ASCO/CAP Guideline Recommendations for Human Epidermal Growth Factor Receptor 2 Testing in Breast Cancer, J. Clinical Oncology, vol. 25, No. 1, p. 118-45 (Dec. 11, 2006).
"Affymetrix GeneChip Human Genome U133 Array Set HG-U133A", GEO, Mar. 11, 2002.
"Tumor Grade", NIH FactSheet, May 19, 2004, retrieved from the Internet: URL:http://www.cancer.gove/cancertopics/factsheet/detection/Fs5_9.pdf.
Ortiz-Martinez et al., "Association of increased osteopontin and splice variant-c mRNA expression with HER2 and triple-negative/basal-like breast carcinomas subtypes and recurrence," Human Pathology, vol. 45, Issue 3, pp. 504-512 (e-published Oct. 30, 2013).
Weber et al., "Categorical meta-analysis of Osteopontin as a clinical cancer marker," Oncology Reports, vol. 25, Issue 2, pp. 433-441 (Feb. 2011).
Pang et al., "Prognostic values of osteopontin-c, E-cadherin and b-catenin in breast cancer," Cancer Epidemiology, vol. 37, Issue 6, pp. 985-992 (e-published Sep. 2013).
Patani et al., "Osteopontin C mRNA expression is associated with a poor clinical outcome in human breast cancer," International Journal of Cancer, vol. 122, Issue 11, pp. 2646 (Jun. 2008).
Patani et al., "Osteopontin Expression Profiles Predict Pathological and Clinical Outcome in Breast Cancer," Anticancer Research, vol. 28, Issue 6B, pp. 4105-4110 (Nov.-Dec. 2008).
Weber et al., "Osteopontin is a marker for cancer aggressiveness and patient survival," British Journal of Cancer, vol. 103, Issue 6, pp. 861-869 (Sep. 2010).
Mirza et al., "Osteopontin-c is a selective marker of breast cancer," International Journal of Cancer, vol. 122, Issue 4, pp. 889-897 (e-published Oct. 24, 2007).
Zduniak et al., "Nuclear osteopontin-c is a prognostic breast cancer marker," vol. 112, Issue 4, pp. 729-738 (e-published Jan. 2015).
Hartung & Weber, "RNA blood levels of osteopontin splice variants are cancer markers," SpringerPlus, 2:110 (Mar. 2013).

* cited by examiner

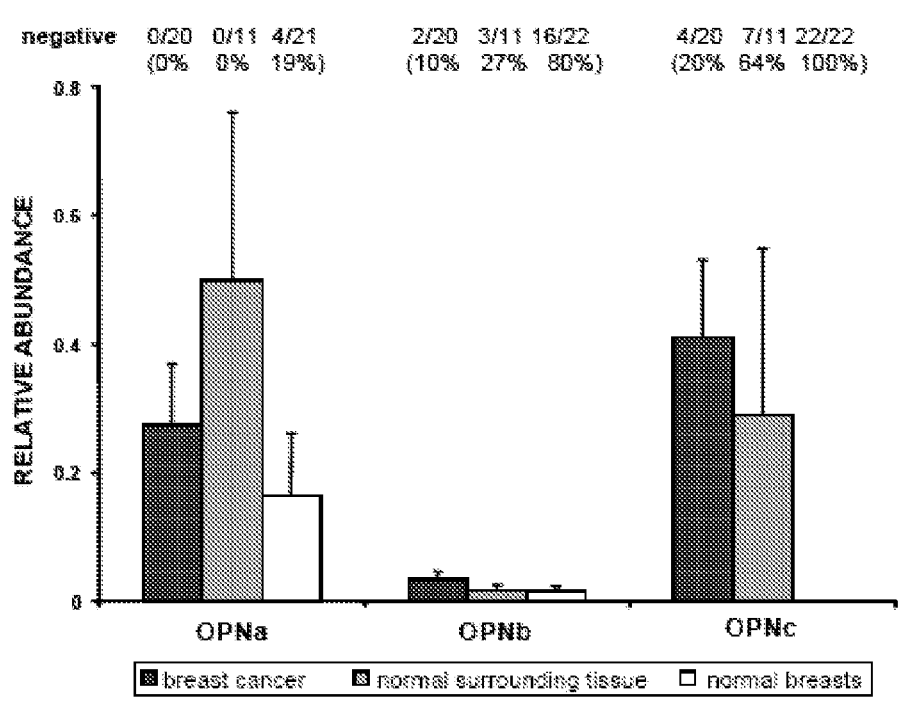
FIG. 1A
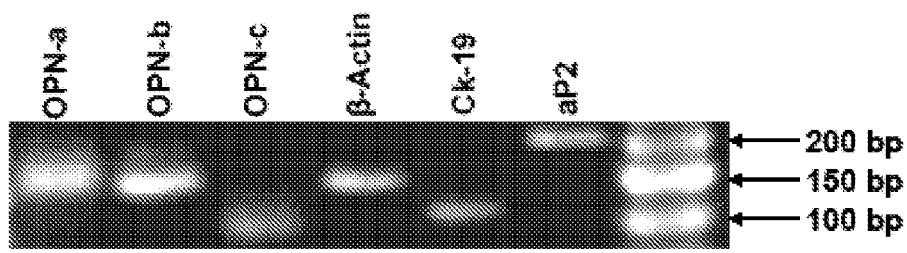
FIG. 1B
FIG. 1C

GRADING, STAGING AND PROGNOSING CANCER USING OSTEOPONTIN-C

CROSS REFERENCE TO RELATED APPLICATION

This application claims priority to U.S. Provisional Application No. 60/980,379 filed Oct. 16, 2007, which is herein incorporated by reference.

ACKNOWLEDGMENT OF GOVERNMENT SUPPORT

This study was supported by Department of Defense breast cancer grant DAMD17-02-0510 and USPHS grant M01 RR 08084 from the General Clinical Research Centers Program, National Center for Research Resources, NIH. Therefore, the United States Government has certain rights to this invention.

FIELD

This application relates to methods for grading, staging, and prognosticating cancers, such as breast cancer, for example ductal carcinoma in situ (DCIS) or lobular carcinoma in situ (LCIS), and kits that can be used for such methods.

BACKGROUND

Around 20% of women who undergo breast biopsy procedures are diagnosed with breast cancer on the basis of conventional histological evaluation. Most biopsies are obtained with a core needle, and sampling or interpretation error may understate the disease identified. Furthermore, the early stages of breast cancer (ductal carcinoma in situ (DCIS) or lobular carcinoma in situ (LCIS)) are difficult to differentiate from benign growths on one end of the spectrum and invasive cancers on the other end. There is a 30-50% risk that DCIS, if not treated, will progress to breast carcinoma. Currently, there are no molecular markers at hand that identify this fraction of high risk DCIS cases. This makes it difficult to decide whether a patient should be treated with lumpectomy, lumpectomy plus radiation or hormone therapy, or resection of the entire breast. While research has identified a large number of biomolecules to be deregulated or defective in breast cancer, relatively few of them are commonly used in histological diagnosis. Specifically, markers that predict invasiveness have not been firmly established. Better molecular predictors of progression are needed to facilitate rational treatment decisions.

Several markers are commonly used in breast cancer diagnosis. The U.S. Food and Drug Administration-approved and ASCO-recommended tumor markers CA15.3, CA27.29, and CEA are useful only for monitoring the therapy of advanced breast cancer or its recurrence. These serum markers still lack the adequate sensitivity (below 25%) and specificity (below 70%) to be applicable in detecting early stage breast carcinoma in a large population [1, 2]. Estrogen receptor (ER) and progesterone receptor (PR) facilitate decisions on therapy, but are weak prognostic measures [2-4]. HER2 over-expression is associated with poor prognosis, but this mechanism underlies only about one third of breast cancers.

Few tumor markers are under study as predictors of breast cancer progression. The transcript and protein of the polycomb group transcriptional repressor EZH2 are consistently elevated in invasive breast carcinoma compared with normal breast epithelia. The EZH2 protein levels are strongly associated with breast cancer aggressiveness [5]. VEGF correlates strongly with uPA in the node-positive population. Patients with high VEGF levels display poor outcome, with an increased risk for the node-positive subset. Furthermore, infiltrating ductal carcinomas express higher levels of both uPA and VEGF than intralobular carcinomas [6]. Multiple malignant breast cancer cell lines over-express the metastasis gene osteopontin, and transfection of this gene into benign tumorigenic breast epithelial cell lines conveys invasive behavior [7]. Consequently, osteopontin has been identified as a prognostic marker associated with patient survival. However, osteopontin may also be present in non-tumorous tissue and in the plasma of healthy individuals [8, 9].

Osteopontin may serve as a cytokine and as an extracellular matrix molecule. It can support migration and protect from programmed cell death after ligation of certain integrin receptors or a CD44 variant on the cell surface. The biological functions of metastasis-associated gene products are extensively regulated on the post-transcriptional and post-translational levels [10]. Consistently, osteopontin secreted from various cells has diverse structural characteristics [11, 12] and tumor-derived osteopontin forms are smaller than osteopontin secreted by non-transformed cells [13]. Transcripts for three osteopontin splice variants are expressed in invasive, but not in non-invasive, breast tumor cell lines [14].

Alternative splicing of osteopontin occurs upstream of the central integrin binding domain and the C-terminal CD44 binding domain. Osteopontin-b lacks exon 5 and osteopontin-c lacks exon 4.

SUMMARY

While the acquisition of invasiveness is a critical step in early stage breast carcinomas (such as CIS), no established molecular markers reliably identify tumor progression. The metastasis gene osteopontin (OPN) is subject to alternative splicing, which yields three messages, osteopontin-a (OPN-a), osteopontin-b (OPN-b), and osteopontin-c (OPN-c). It is shown herein that OPN-c is a biomarker for breast cancer. The RNA message for OPN-c was present in 16 of 20 breast cancers (80%), but was undetectable in 22 normal specimens obtained from reduction mammoplasty. In contrast, OPN-a RNA was expressed at various levels in all 20 breast cancers, eleven tumor-surrounding tissues, and 21 normal samples. The splice variant OPN-b was present at barely detectable levels in 18 of 20 cancers and in six of 22 normal breasts. By immunohistochemistry, 66 of 69 normal breasts were negative, while three showed low level staining Among the breast cancers, 43 of 56 cores (77%) stained positive for OPN-c. When correlated with tumor grade, the staining for OPN-c increased from grade 1 to grade 3. OPN-c detects a higher fraction of breast cancers than estrogen receptor (ER), progesterone receptor (PR), or human epidermal growth factor receptor 2 (HER2). In 178 breast specimens analyzed, OPN-c was present in 78% of cancers, 36% of surrounding tissues, and 0% of normal tissues. Therefore, OPN-c can serve as a selective diagnostic and prognostic marker for breast cancer. It can also be used in a diagnostic panel together with conventional breast cancer markers such as ER, PR and HER2.

Based on these observations, methods for grading, staging, and or prognosticating breast cancer (such as CIS), or other tumor that expresses osteopontin (such as OPN-c), in a subject are provided. In particular examples the method includes detecting or measuring OPN-c in a breast or other cancer sample, wherein the presence of relatively high OPN-c levels indicates that the subject has a higher grade (e.g., a more aggressive form of) breast or other cancer, such as a grade 3 breast cancer. In contrast, if relatively low OPN-c levels are detected in the breast or other cancer sample, this indicates that the subject has a lower grade (e.g., a less aggressive form of) breast or other cancer, such as grade 1. In some examples, when referring to tumor grades herein (i.e., grade scale of 1-3) the tumor grading is as per the Scarff-Bloom-Richardson system [15, herein incorporated by reference as to the grading method and descriptions]. However, one skilled in the art will appreciate that other methods can be used, and that variations in scoring may occur between samples or when different detection reagents are used. In some examples, the greater the amount of OPN-c detected (e.g., 3 on a scale of 0 to 3) indicates that the subject has a higher grade (or more aggressive form of) breast or other cancer, such as a grade 3 cancer, while the lower the amount of OPN-c detected (e.g., 1 on a scale of 0 to 3) indicates that the subject has a lower grade (or less aggressive form of) breast or other cancer, such as grade 1. Any method of detecting OPN-c can be used, such as methods that permit detection of OPN-c proteins (e.g., by using OPN-c antibodies) or OPN-c nucleic acid molecules (e.g., by using OPN-c nucleic acid probes or primers).

The method can further include detecting or measuring one or more other cancer markers in the sample, such as the breast cancer markers ER; PR; and/or HER2. For example, low levels of ER or high levels of HER2 and significantly elevated OPN-c (an in some examples also low PR) in the breast cancer sample indicates that the subject a grade 2 or 3 breast cancer while lower levels of OPN-c and in some examples also lower levels of HER2 (and in some examples if the sample is also ER+ and/or PR+) in the breast cancer sample indicates that the subject has a grade 1 breast cancer.

Based on the results of the method, a treatment protocol can be selected for the subject. Currently, there is no particular treatment regimen for a subject who is shown to be OPN-c positive. However, based on the data provided herein, subjects shown to have a more aggressive form of breast or other cancer (for example even if they are negative for ER, PR, or HER2) can receive a more aggressive therapy (such as one or more of mastectomy, chemotherapy, radiation) than subjects shown to have a less aggressive form of the cancer.

In particular examples, the method has a sensitivity of at least 80% and a specificity of at least 80%, such as a sensitivity of at least 90% and a specificity of at least 90%.

The present disclosure also provides kits that can be used for breast or other cancer diagnosis, staging, grading, or combinations thereof. For example, such kits can be used to identify a subject having aggressive or less aggressive forms of breast cancer. In particular examples, such kits include or consist of specific binding agents (such as antibodies) that bind to one or more of ER, PR, HER2, and OPN-c. In some examples, the kits include or consist of nucleic acid primers or probes specific for OPN-c, ER, PR, and HER2. The kits can also include one or more control samples (such as positive and negative control samples) whose detectable levels of ER, PR, HER2 and/or OPN-c and/or grade of breast cancer are known.

The foregoing and other objects and features of the disclosure will become more apparent from the following detailed description, which proceeds with reference to the accompanying figures.

BRIEF DESCRIPTION OF THE DRAWINGS

FIGS. 1A-C: OPN splice variant expression in breast tissue. A) RNA was analyzed by real-time RT-PCR from snap frozen tissue samples. The data are presented as mean±SEM. The total number of samples and the number of samples with undetectable levels of osteopontin over 40 cycles of amplification is indicated above the graph. B) Representative agarose gel with the real-time RT-PCR products of a tumor specimen. C) Reproducibility of real time RT-PCR amplification. MDA-MB-435 cells, known to express OPN-a and the splice variants -b and -c [14], were used as control for calculating the expression of osteopontin forms in the tissue. β-actin served as a reference gene and relative expression ratios of the target gene were calculated from the cycle threshold and efficiency measurements (Pfaffl, *Nucleic Acids Res* 29:e45, 2001). Repeated thawing of cDNA degrades the messages for osteopontin splice variants faster than the message for β-actin. The breast specimens were obtained and analyzed over two time periods interrupted by a break of several months. The scatters of the reference values within each time period were tighter than the combined ranges, possibly reflecting a small influence by batch-to-batch variations in the reagents used for RNA extraction, reverse transcription, and amplification.

SEQUENCE LISTING

Figure 2A:
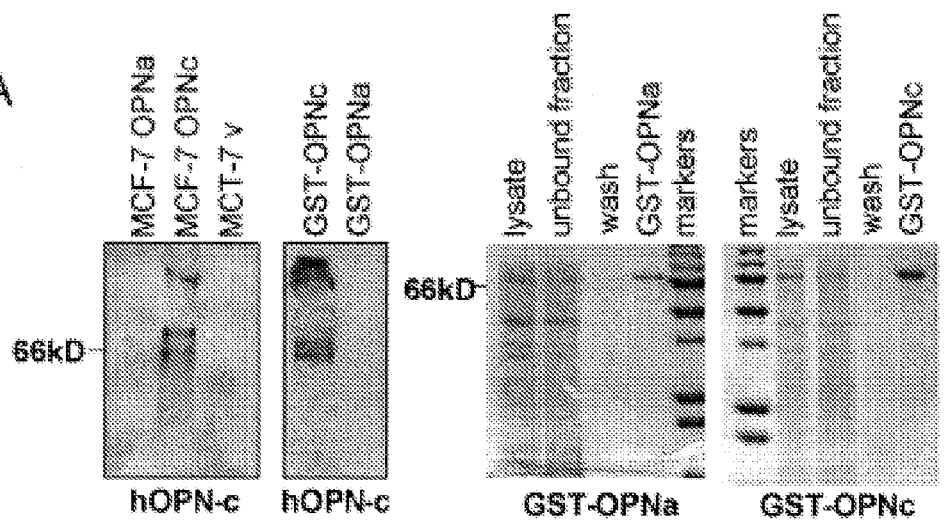
FIGS. 2A-C: Antibody characterization. A) Specificity of anti-hOPNc IgY. Hens were immunized with a peptide representing the splice junction of human OPN-c. To mimic an internal sequence, the peptide was N-terminally acetylated. At the end of the immunization period, total immunoglobulin (IgY) was purified from eggs and used for Western blotting. Left panel: supernatants from transfected MCF-7 cells probed with the anti-hOPNc antibody (a prior Western blot of the same supernatants had demonstrated the comparable expression levels of OPN-a and -c). Right panel: 400 ng of GST-OPN was loaded per lane, probed with the anti-hOPNc antibody. The additional band around 120 kD is commonly observed for osteopontin and likely reflects an aggregated form of the molecule. The purity of the GST-OPN fusion proteins is shown on the Coommassie gel. Osteopontin-a and -c were amplified by PCR by exclusion of the signal peptide (amino acids 1-17). The amplified fragments were subcloned into pGEX-5T vector and transformed into BL21 bacteria for protein synthesis. Reading frames and sequence fidelity were confirmed by sequencing analysis. The proteins were purified from bacterial lysates by pull-down with GSH-Sepharose. B) Immunocytochemistry of cell lines with known OPN expression levels. MCF-7 cells and ZR-75 cells are non-invasive and do not express osteopontin, MDA-MB-435 cells are metastatic in vivo and express all three osteopontin splice variants [14]. C) Staining of breast cancer tissue with the IgY antibody to osteopontin-c (top left) or with a rabbit antibody to a common region of all splice variants (O-17, Assay Designs Inc.) (bottom left). The negative controls (top and bottom right) reflect the work-up without the primary antibody.

The nucleic and amino acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. In the accompanying sequence listing:

SEQ ID NOS: 1 and 2 are exemplary forward and reverse primers, respectively, that can be used to amplify OPN-a.

SEQ ID NOS: 3 and 4 are exemplary forward and reverse primers, respectively, that can be used to amplify OPN-b.

SEQ ID NOS: 5 and 6 are exemplary forward and reverse primers, respectively, that can be used to amplify OPN-c.

SEQ ID NOS: 7 and 8 are exemplary forward and reverse primers, respectively, that can be used to amplify β-actin.

SEQ ID NOS: 9 and 10 are exemplary forward and reverse primers, respectively, that can be used to amplify Ck-19.

SEQ ID NOS: 11 and 12 are exemplary forward and reverse primers, respectively, that can be used to amplify aP2.

SEQ ID NOS: 13 and 14 are exemplary forward and reverse primers, respectively, that can be used to amplify GAPDH.

SEQ ID NOS: 15 and 16 are exemplary forward and reverse primers, respectively, that can be used to amplify the osteopontin coding sequence.

DETAILED DESCRIPTION

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising an antibody" includes single or plural antibodies and is considered equivalent to the phrase "comprising at least one antibody." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank Accession Nos. referred to herein are the sequences available at least as early as Oct. 15, 2007, and are hereby incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

CIS: carcinoma in situ
DCIS: ductal carcinoma in situ
ER: estrogen receptor
HER2: human epidermal growth factor receptor 2
LCIS: lobular carcinoma in situ
OPN: osteopontin
PR: progesterone receptor Antibody: Immunoglobulin molecules and immunologically active portions of immunoglobulin molecules, that is, molecules that contain an antigen binding site that specifically binds (immunoreacts with) an antigen (such as OPN-c, ER, PR, or HER2). Exemplary antibodies include monoclonal, polyclonal, and humanized antibodies.

A naturally occurring antibody (such as IgG, IgM, IgD) includes four polypeptide chains, two heavy (H) chains and two light (L) chains interconnected by disulfide bonds. As used herein, the term antibody also includes recombinant antibodies produced by expression of a nucleic acid that encodes one or more antibody chains in a cell (for example see U.S. Pat. No. 4,745,055; U.S. Pat. No. 4,444,487; WO 88/03565; EP 256,654; EP 120,694; EP 125,023; Faoulkner et al., Nature 298:286, 1982; Morrison, J. Immunol. 123: 793, 1979; Morrison et al., Ann Rev. Immunol 2:239, 1984).

The term antibody also includes an antigen binding fragment of a naturally occurring or recombinant antibody. Specific, non-limiting examples of binding fragments encompassed within the term antibody include Fab, (Fab')$_2$, Fv, and single-chain Fv (scFv). Fab is the fragment that contains a monovalent antigen-binding fragment of an antibody molecule produced by digestion of whole antibody with the enzyme papain to yield an intact light chain and a portion of one heavy chain or equivalently by genetic engineering. Fab' is the fragment of an antibody molecule obtained by treating whole antibody with pepsin, followed by reduction, to yield an intact light chain and a portion of the heavy chain; two Fab' fragments are obtained per antibody molecule. (Fab')$_2$ is the fragment of the antibody obtained by treating whole antibody with the enzyme pepsin without subsequent reduction or equivalently by genetic engineering. F(Ab')$_2$ is a dimer of two FAb' fragments held together by disulfide bonds. Fv is a genetically engineered fragment containing the variable region of the light chain and the variable region of the heavy chain expressed as two chains. Single chain antibody ("SCA") is a genetically engineered molecule containing the variable region of the light chain, the variable region of the heavy chain, linked by a suitable polypeptide linker as a genetically fused single chain molecule. Methods of making these fragments are routine in the art.

Binding affinity: Affinity of an antibody for an antigen, such as the affinity of an antibody for an OPN-c peptide. In one example, affinity is calculated by a modification of the Scatchard method described by Frankel et al., *Mol. Immunol.*, 16:101-106, 1979. In another example, binding affinity is measured by an antigen/antibody dissociation rate. In yet another example, a high binding affinity is measured by a competition radioimmunoassay. In several examples, a high binding affinity is at least about $1\times10^{-8}$ M. In other example, a high binding affinity is at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about $5.0\times10^{-8}$ M.

Breast cancer: Includes any tumor of the breast, such as tumors of epithelial (carcinoma) or stromal (sarcoma) breast tissue. Exemplary in situ epithelial breast cancers include DCIS and LCIS. Lobular carcinoma in situ (LCIS) is a tumor that consists of abnormal cells in the lining of a lobule. Subjects having LCIS means that the subject has an increased risk of developing breast cancer in either breast. Ductal carcinoma in situ (DCIS) is made up of abnormal cells in the lining of a duct. It is a pre-invasive malignant tumor, and is also called intraductal carcinoma. The abnormal cells have not yet spread beyond the duct and have not yet invaded the surrounding breast tissue. DCIS is sometimes called Stage 0 breast cancer because it is not invasive. Exemplary invasive breast carcinomas include carcinoma NOS (not otherwise specified), lobular carcinoma, tubular/cribriform carcinoma, mucinous (colloid) carcinoma, medullary carcinoma, papillary carcinoma, and metaplastic carcinoma. An exemplary breast sarcoma is phyllodes tumour.

Contact: To bring one agent into close proximity to another agent, thereby permitting the agents to interact. For example, an antibody can be applied to a microscope slide or other surface containing a biological sample, thereby permitting detection of one or more proteins in the sample that are specific for the antibody.

Detect: To determine if an agent is present or absent. In some examples this can further include quantification. For example, use of an antibody specific for a particular protein (e.g., OPN-c, ER, PR, or HER2) permits detection of the protein in a sample, such as a sample containing breast cancer tissue. In particular examples, an emission signal from a fluorophore (such as an increase in the signal) is detected.

Detection can be in bulk, so that a macroscopic number of molecules (such as at least $10^{23}$ molecules) can be observed simultaneously. Detection can also include identification of signals from single molecules using microscopy and such techniques as total internal reflection to reduce background noise.

Estrogen receptor (ER): A member of the nuclear hormone family of intracellular receptors is activated by 17β-estradiol. Estrogen receptors, such as ERα, are overexpressed in around 70% of breast cancer cases, referred to as "ER positive" (ER+). There are two different forms of the estrogen receptor, usually referred to as α and β, each encoded by a separate gene (ESR1 and ESR2 respectively). ERα (OMIM 133430), expressed from the ESR1 gene, is found in endometrium, breast cancer cells, ovarian stroma cells and in the hypothalamus. Therefore, in particular examples ER refers to the ERα form found in breast cancer cells.

Estrogen receptor sequences are publicly available. For example, GenBank Accession Nos: BC128574.1 (nucleic acid) and P03372.2 (protein) disclose human ERα sequences and Nos. NM_007956.4 (nucleic acid) and P19785.1 (protein) disclose mouse ERα sequences. In one example, an ER sequence includes a full-length wild-type (or native) sequence, as well as variants (e.g., polymorphisms) found in breast cancer cells. In certain examples, ER has at least 80% sequence identity, for example at least 85%, at least 90%, at least 95%, or at least 98% sequence identity to a native ERα (such as the sequence of GenBank Accession Nos: P03372.2, BC128574.1, NM_007956.4 and P19785.1) and retains ERα activity (e.g., expressed in breast cancer cells). In other examples, an ER nucleic acid sequence has a sequence that hybridizes under very high stringency conditions to a sequence set forth in GenBank Accession No. BC128574.1 or NM_007956.4 and is expressed in breast cancer cells.

Grading cancer: A cancer can be graded according to its level of differentiation. The lower the number, the lower the grade, and the slower the cancer is growing. Cancers are usually graded on a scale of 1 to 3. Grade 1 indicates the cancer cells look similar to normal cells, and the cancer is likely to be less aggressive. Grade 2 indicates the cancer cells appear dysplastic, and are more likely to be aggressive and grow faster. Grade 3 cancer cells highly dysplastic and are more likely to be very aggressive in growth.

Human epidermal growth factor receptor 2 (HER2): A member of the ErbB protein family, which is a proto-oncogene. In humans, the HER2 gene is located at the long arm of human chromosome 17(17q11.2-q12). Approximately 25-30% of breast cancers have an amplification of the HER2/neu gene or overexpression of its protein product, referred to as "HER2 positive" (HER2+). HER2+ patients can receive the monoclonal antibody trastuzumab (Herceptin) as a therapy for breast cancer. Overexpression of HER2 in breast cancer has been associated with increased disease recurrence and worse prognosis.

HER2 sequences are publicly available. For example, GenBank Accession Nos: NM_001005862.1 and NM_004448.2 (nucleic acid) and NP_001005862.1 and NP_004439.2 (protein) disclose human HER2 sequences. In one example, a HER2 sequence includes a full-length wild-type (or native) sequence, as well as HER2 variants (e.g., polymorphisms) found in breast cancer cells. In certain examples, HER2 has at least 80% sequence identity, for example at least 85%, at least 90%, at least 95%, or at least 98% sequence identity to a native HER2 (such as the sequence of GenBank Accession Nos: NM_001005862.1, NM_004448.2, NP_001005862.1 and NP_004439.2) and retains HER2 activity. In other examples, a HER2 nucleic acid sequence has a sequence that hybridizes under very high stringency conditions to a sequence set forth in GenBank Accession No. NM_001005862.1 or NM_004448.2 and retains HER2 activity.

Label: An agent capable of detection, for example by spectrophotometry, flow cytometry, or microscopy. For example, one or more labels can be attached to an antibody, thereby permitting detection of the target protein. In another example, one or more labels can be attached to a nucleic acid probe, thereby permitting detection of the target nucleic acid molecule. Exemplary labels include radioactive isotopes, fluorophores, ligands, chemiluminescent agents, enzymes, and combinations thereof.

Normal cells or tissue: Non-tumor, non-malignant cells and tissue.

Nucleic acid molecules: A deoxyribonucleotide or ribonucleotide polymer including, without limitation, cDNA, mRNA, genomic DNA, and synthetic (such as chemically synthesized) DNA. The nucleic acid molecule can be double-stranded or single-stranded. Where single-stranded, the nucleic acid molecule can be the sense strand or the antisense strand. In addition, nucleic acid molecule can be circular or linear. The disclosure includes methods that detect OPN-c, ER, PR, and HER2 nucleic acid molecules.

Osteopontin-c (OPN-c): Osteopontin is a secreted multi-functional phosphorylated glycoprotein expressed at high levels in tumors, including those of the breast. Several splice variants of OPN have been identified, including OPN-a (native sequence), OPN-b (truncated sequence) and OPN-c (truncated sequence). OPN-c lacks exon 4 (27 amino acids) in the $NH_2$-terminal region of the mature sequence. OPN-c lacks the transglutaminase reactive domain (Gly-X-Gly) which can mediate covalent homodimer cross-linking as well as heterodimer formation to other matrix components (such as fibronectin).

OPN-c sequences are publicly available. For example, GenBank Accession Nos: D28761 (nucleic acid) and BAA05951 (protein) disclose human OPN-c sequences. In one example, an OPN-c sequence includes a wild-type (or native) sequence, as well as OPN-c variants (e.g., polymorphisms) expressed in breast cancer cells. In certain examples, OPN-c has at least 80% sequence identity, for example at least 85%, at least 90%, at least 95%, or at least 98% sequence identity to a native OPN-c (such as the sequence of GenBank Accession Nos: D28761 and BAA05951). In other examples, an OPN-c nucleic acid sequence has a sequence that hybridizes under very high stringency conditions to a sequence set forth in GenBank Accession No. D28761 and retains OPN-c activity.

Primer: Short nucleic acid molecules, for instance DNA oligonucleotides 10-100 nucleotides in length, such as about 15, 20, 25, 30 or 50 nucleotides or more in length, such as this number of contiguous nucleotides of a OPN-c, ER, PR, or HER2 nucleic acid molecule (e.g., gene, cDNA, or mRNA sequence). Primers can be annealed to a complementary target DNA strand by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length.

In one example, a primer includes at least 15 consecutive nucleotides of an OPN-c, ER, PR, or HER2 nucleic acid molecule, such as at least 18 consecutive nucleotides, at least 20, at least 25, at least 30, at least 35, at least 40, at least 45, at least 50 or more consecutive nucleotides of an OPN-c, ER, PR, or HER2 nucleotide sequence. Such primers can be used to amplify OPN-c, ER, PR, or HER2, for example using PCR.

Probe: A short sequence of nucleotides, such as at least 8, at least 10, at least 15, at least 20, at least 21, at least 25, or at least 30 nucleotides in length (e.g., 8 to 40 or 10 to 30 nucleotides), used to detect the presence of a complementary sequence (such as a OPN-c, ER, PR, or HER2 nucleic acid sequence), for example by molecular hybridization. Ideally, a probe that is specific for a particular nucleic acid sequence (e.g., an OPN-c sequence) does not significantly hybridize to other nucleic acid sequences (e.g., non-OPN-c sequences) under highly stringent conditions. In particular examples, oligonucleotide probes include a label that permits detection of oligonucleotide probe:target sequence hybridization complexes. For example, an oligonucleotide probe can include these numbers of contiguous nucleotides of an OPN-c, ER, PR, or HER2 nucleic acid molecule (e.g., gene, cDNA, or mRNA sequence), along with a detectable label. Such an oligonucleotide probe can be used to detect the presence of the OPN-c, ER, PR, or HER2 nucleic acid molecule in a sample.

Progesterone receptor (PR): An intracellular steroid receptor that specifically binds progesterone. Progesterone receptors are overexpressed in some breast cancer cases, referred to as "PR positive" (PR+).

The term progesterone receptor (OMIM: 607311) includes those progesterone receptor genes (PGR) found in mammals and retains progesterone receptor biological activity. Progesterone receptor sequences are publicly available. For example, GenBank Accession Nos: AF016381.1 (nucleic acid) and AAD01587.1 (protein) disclose human PR sequences and Nos. M68915.1 (nucleic acid) and AAA39971.1 (protein) disclose mouse PR sequences. In one example, a PR sequence includes a full-length wild-type (or native) sequence, as well as PR variants (e.g., polymorphisms) that retain PR biological function (e.g., ability to bind progesterone). In certain examples, PR has at least 80% sequence identity, for example at least 85%, at least 90%, at least 95%, or at least 98% sequence identity to a native PR (such as the sequence of GenBank Accession Nos: AF016381.1, AAD01587.1, M68915.1 and AAA39971.1) and retains PR activity. In other examples, a PR nucleic acid sequence has a sequence that hybridizes under very high stringency conditions to a sequence set forth in GenBank Accession No. AF016381.1 or M68915.1 and retains PR activity.

Quantify: To express as a numerical amount, whether an actual amount or a relative amount.

Sample: A biological specimen containing genomic DNA, RNA (including mRNA), protein, or combinations thereof, obtained from a subject. Examples include, but are not limited to, peripheral blood, urine, saliva, tissue biopsy, surgical specimen, and autopsy material. In some examples, the sample is a tissue sample obtained from a subject known to have, or suspected to have, cancer. In one example, a sample includes breast tissue, such as that obtained during a needle biopsy, lumpectomy, or mastectomy. Samples, such as tissue samples, can be placed on microscope slides. In particular examples, samples are used directly, or can be manipulated prior to use, for example, by fixing (e.g., using formalin) or embedding (e.g., in plastic or paraffin).

Specific binding agent: An agent that binds substantially only to a defined target. Thus an OPN-c specific binding agent is an agent that binds substantially to an OPN-c peptide or nucleic acid molecule. In one example, the specific binding agent is an antibody that specifically binds an OPN-c peptide.

The term "specifically binds" refers, with respect to an antigen such as OPN-c, to the preferential association of an antibody or other specific binding agent, in whole or part, to the antigen and not to other antigens. A certain degree of non-specific interaction can occur between a specific binding agent and a non-target antigen. Nevertheless, specific binding can be distinguished as mediated through specific recognition of the antigen. Specific binding results in a significant association between the antibody (or other specific binding agent) and the antigen than between the antibody and a non-antigen. Specific binding typically results in greater than 2-fold, such as greater than 5-fold, greater than 10-fold, or greater than 100-fold increase in amount of bound antibody or other specific binding agent to the antigen as compared to binding to a non-specific antigen.

The determination that a particular agent binds substantially only to OPN-c or other protein (e.g., ER, PR, or HER2) can be made using or adapting routine procedures. For example, western blotting can be used to determine that a specific binding agent, such as an antibody, binds substantially only to the protein (such as substantially only binds OPN-c but not to other proteins in a breast cancer cell) (for example see Harlow and Lane, *Antibodies: A Laboratory Manual.* 1988). A variety of immunoassay formats are appropriate for selecting antibodies or other specific binding agent specifically immunoreactive with a particular protein (such as OPN-c). For example, solid-phase ELISA immunoassays are routinely used to select monoclonal antibodies specifically immunoreactive with a protein.

Staging cancer: A cancer, such as breast cancer, can be staged to describe the extent or severity of a cancer based on the extent of the original (primary) tumor and the extent of spread in the body. Staging considers the primary tumor (T), the regional lymph nodes (N), and distant metastases (M). The size of the primary tumor and the extent of regional lymph node metastases are usually staged on a scale from 0 to 4. Metastases are staged as 0 (no metastases present) or 1 (metastases present). Low numbers indicate tumors that have spread little, while high numbers refer to tumors that have spread extensively. The TNM classification is most commonly used (see the AJCC Staging Manual), where T describes the size of the tumor and whether it has invaded nearby tissue, N describes any lymph nodes that are involved, and M describes metastasis (spread of cancer from one body part to another). However, other classification frameworks for staging cancer are within the scope of this disclosure.

In particular examples, the stages of breast cancer are as follows: Stage 0—carcinoma in situ; Stage I—Tumor (T) does not involve axillary lymph nodes (N); Stage IIA—T 2-5 cm, N negative, or T<2 cm and N positive; Stage IIB—T>5 cm, N negative, or T 2-5 cm and N positive (<4 axillary nodes); Stage IIIA—T>5 cm, N positive, or T 2-5 cm with 4 or more axillary nodes; Stage IIIB—T has penetrated chest wall or skin, and may have spread to <10 axillary N; Stage IIIC—T has >10 axillary N, 1 or more supraclavicular or infraclavicular N, or internal mammary N; and Stage IV—Distant metastasis (M).

Subject: Living multi-cellular vertebrate organisms, a category that includes human and non-human mammals, such as veterinary subjects. In a particular example, a subject is one who had or is suspected of having had breast cancer, such as DCIS.

Target molecule: A biomolecule whose detection or measurement is desired, such as a breast cancer marker. Examples of target molecules include OPN-c, ER, PR, and HER-2.

Tumor: A neoplasm. In one example, a tumor is one that expresses OPN, such as OPN-c. Exemplary tumors that express OPN include but are not limited to adrenocortical cancer, ameloblastoma, ampullary cancer, bladder cancer, bone cancer, breast cancer, cervical cancer, cholangioma, colorectal cancer, endometrial cancer, esophageal cancer, gastric cancer, glioma, granular call tumor, head and neck cancer, hepatocellular cancer, hydatiform mole, lung cancer, lymphoma, melanoma, mesothelioma, myeloma, neuroblastoma, oral cancer, osteochondroma, osteosarcoma, ovarian cancer, pancreatic cancer, pilomatricoma, prostate cancer, renal cell cancer, salivary gland tumor, soft tissue tumors, Spitz naevus, squamous cell cancer, teratoid cancer, and thyroid cancer.

Under conditions sufficient for: A phrase that is used to describe any environment that permits the desired activity (e.g., appropriate time, temperature, reaction conditions). An example includes contacting an antibody or nucleic acid probe with a breast cancer sample sufficient to allow detection of one or more target molecules (e.g., ER, PR, HER2, OPN-c) in the sample and can include quantification of one or more target molecules in the sample.

Methods of Grading and Staging Cancer

It is shown herein that the OPN-c splice variant is expressed in 75-80% of breast carcinomas, but not in normal breast tissues. The levels of OPN-c correlate with tumor grade. This makes OPN-c a marker for the invasive potential of breast tumors, which can permit clinicians to select appropriate treatment regimens for a patient with breast or other cancer. OPN-c is a better breast cancer marker than OPN-a because it is absent from normal breast tissue. In fact, quantitative analysis of the RNA levels did not discern statistically significant differences between normal and tumorous breasts for OPN-a. Based on these results, detection of OPN-c in a tumor sample can be used to grade or stage any OPN-expressing tumor, such as adrenocortical cancer, ameloblastoma, ampullary cancer, bladder cancer, bone cancer, breast cancer, cervical cancer, cholangioma, colorectal cancer, endometrial cancer, esophageal cancer, gastric cancer, glioma, granular call tumor, head and neck cancer, hepatocellular cancer, hydatiform mole, lung cancer, lymphoma, melanoma, mesothelioma, myeloma, neuroblastoma, oral cancer, osteochondroma, osteosarcoma, ovarian cancer, pancreatic cancer, pilomatricoma, prostate cancer, renal cell cancer, salivary gland tumor, soft tissue tumors, Spitz naevus, squamous cell cancer, teratoid cancer, and thyroid cancer.

The lack of reliable molecular indicators for breast cancer progression has led to efforts to use increasingly complex readouts. Multiple tumor markers, including HER2 amplification/over-expression, cathepsin D, and uPAR, have been considered for prognostication and therapy decisions of breast cancer in a Tumor Marker Utility Grading System (Hayes et al., *Breast Cancer Res. Treat.* 52:305-19, 1998). A gene prognosis profile of 70 genes, developed at the Netherlands Cancer Institute, has been characterized as a good predictor of outcome (van de Vijver et al., *N. Engl. J. Med.* 347:1999-2009, 2002). The likelihood of distant recurrence in breast cancer patients, who have estrogen receptor positive tumors and no involved lymph nodes, can be defined with a panel of 21 gene products, amplified by RT-PCR from paraffin blocks, and correlated with the likelihood of distant recurrence (Paik et al., *N. Engl. J. Med.* 351:2817-2826, 2004). The selective expression of OPN-c in breast cancers, but not in healthy breasts, can provide a simpler and comparably reliable diagnostic and prognostic marker.

The disclosed methods and kits can provide additional treatment options. For example, if a subject is positive for ER, PR or HER2, there are standard treatment regimens (e.g., Herceptin for HER2+ or tamoxifen for ER+ or PR+). However, for subjects that are negative for all three of ER, PR and HER2, there is no current method to determine how these subjects will progress. It is shown herein that at least 38% of subjects who are negative for ER, PR and HER2 are highly positive for OPN-c, and the OPN-c highly positive subjects are those having more aggressive cancers (e.g., grade 2 and 3). Therefore, the disclosure provides methods of selecting patients having breast or other cancers that are highly OPN-c positive for additional, more aggressive therapies (such as a mastectomy instead of a lumpectomy or a lumpectomy combined with chemotherapy (such as Herceptin® therapy if the tumor overexpresses HER2 and tamoxifen or other anti-estrogen therapy if the tumor overexpresses ER) instead of a lumpectomy alone).

Provided herein are methods of grading and/or staging an OPN-expressing cancer, such as breast cancer, for example DCIS or LCIS. In some examples, the cancer is a breast cancer is known to be ER−(ER negative), PR−, and HER2−. The method can include detecting or measuring the OPN-c expression level in a breast or other cancer sample obtained from the subject, wherein the presence of significant amounts of detectable OPN-c in the breast cancer or other cancer sample (e.g., top ⅓ intensity or top ⅔ intensity) indicates that the subject has more aggressive cancer (such as a higher grade, such as grade 2 or 3 breast cancer), the presence of moderate amounts of detectable OPN-c (e.g., mid-⅓ intensity) in the breast or other cancer sample indicates that the subject has a moderately aggressive cancer (such as a grade 2 breast cancer), while the presence of lower amounts of detectable OPN-c (e.g., lower ⅓ intensity) in the breast or other cancer sample indicates that the subject has a less aggressive cancer (such as a lower grade, such as grade 1 breast cancer). In some examples, the method further includes selecting a subject having or suspected of having breast or other cancer that expresses OPN (such as OPN-c).

In some examples, the level of OPN-c expression is quantified or scaled, and may optionally be compared to a control or reference value (or range of values) of OPN-c expression (such as a positive or negative cancer control, or a particular grade of tumor). Quantification does not require determining an absolute amount, but can include determining a relative amount. For example, the relative or absolute quantity of OPN-c in a sample can be determined. In some examples, the relative amount of OPN-c present is determined, for example by quantifying the amount of OPN-c present. In some examples, OPN-c expression levels are normalized, for example normalized by comparing OPN-c expression to a control (e.g., the level of expression of a housekeeping gene such as β-actin or GAPDH) in the tumor sample. In some examples, OPN-c (and in some examples other cancer markers or housekeeping genes known in the art) is also detected or measured in normal tissue, or in non-cancerous tissue adjacent to cancer tissue. For example, normal breast tissue can serve as a negative or background control for OPN-c, as OPN-c is not expressed in normal breast tissue (see FIG. 1A).

In one example, immunohistochemistry (IHC) is used to detect OPN-c (and other cancer markers). In some examples when IHC is used, the scale of detectable staining is represented on a typical 1+ to 3+ scale to represent the intensity, wherein 0 is assigned to negative staining, 3 being assigned to very intensely staining samples, and 1 assigned to weakly staining samples (see Table 1). In some examples a value of 2 is re-tested. Therefore, in particular examples, if a level of "1" is detected for OPN-c, this indicates that the subject has a less aggressive cancer (such as a grade 1 breast cancer or a stage 0-I breast cancer), while detection of a level "3" for OPN-c indicates that the subject has an aggressive cancer (such as a grade 2 or 3 breast cancer or a stage II or higher breast cancer). For example, as shown in Table 1, tumors can be graded depending on their relative level of OPN-c expression. One skilled in the art will appreciate that these values are not absolutes and can vary depending on the samples and reagents used.

TABLE 1

Exemplary correlation of OPN-c staining intensity to tumor grade.

| Report Result | Staining Intensity Score | Microscope Observation | Tumor Grade |
|---|---|---|---|
| Positive: Any IHC staining of tumor cell membranes above background level whether it is complete or incomplete circumferential staining in more than 0% tumor cells | 3+ | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present. | 3 |
| | 2.5 | Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. | 2 |
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also | 2 |

TABLE 1-continued

Exemplary correlation of OPN-c staining intensity to tumor grade.

| Report Result | Staining Intensity Score | Microscope Observation | Tumor Grade |
|---|---|---|---|
| | | considered 2+. The cytoplasmic reactivity is of weaker intensity than the membrane reactivity. | |
| | 1.5 | Slight reactivity: Staining of intermediate intensity that is membraneous. Cytoplasmic reactivity that is uniform and involves all the cytoplasm may be present, but should not be evaluated for positivity. | 1 |
| | 1+ | Weak reactivity: Faint or light brown reactivity that is membranous. Cytoplasmic reactivity that is uniform and involves all the cytoplasm may be present, but should not be evaluated for positivity. | 1 |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. | 1 |
| | 0 | No reactivity | |

The methods of the present disclosure are not limited to particular methods of representing OPN-c expression levels present in the subject sample. Although the typical 1+ to 3+ scale to represent the signal intensity can be used (for example when IHC is used to detect a target molecule), other scales can be used. In one example, the mean combined score is used to represent the OPN-c levels present in a subject sample. The mean combined score methods can provide a scale ranging from 0 to 300. The tissues are assessed by scoring the cytoplasm using a typical 1+ to 3+ scale to represent the intensity, with 3 being assigned to very intensely staining samples, 1 to weakly staining samples, and 0 to negatively staining samples. Combined pathology scores are calculated from mean intensity (ranging from 1 to 3) multiplied by mean percent (ranging from 0 to 100) of tissue stained. The highest possible score is 300. To assign a tumor grade, the modified Scarff-Bloom-Richardson (SBR) system may be used, which considers nuclear grade, tubule formation, and mitotic rate. The combination of scores for these factors is applied to assign a grade of 1, 2, or 3 (or to assign a particular tumor stage). In some examples, the signal (or value in the range of 0 to 300) obtained from the sample tissue is compared to a control signal (or value or range of values expected from a control sample). For example, the resulting value from the experimental sample in the range of 0 to 300 can be compared to control samples having known tumor grades (or normal tissue) and their resulting values on the 0 to 300 sale, or can be compared to expected values on the 0 to 300 scale for each tumor grade (or stage). For example if a control grade 3 tumor has a range of 250 to 300, control grade 2 tumor has a range of 150 to 249, control grade 1 tumor has a range of 50 to 149, and the normal sample has a range of 0 to 49, if the experimental value obtained is 275 the experimental sample is concluded to be a grade 3 tumor while if the experimental value obtained is 74 the experimental sample is concluded to be a grade 1 tumor. One skilled in the art will appreciate that the values provided above are for demonstration purposes, and that absolute values or ranges of values will vary, for example depending on the method used to detect expression.

Yet other methods that can be used to represent the OPN-c levels present in a subject sample include a continua of numbers, whose absolute value may vary depending on the particular experimental sample and/or the particular control (e.g., particular housekeeping gene) used. Examples of such methods are known in the art (see for example U.S. Pat. Nos. 7,056,674 and 7,081,340; herein incorporated by reference). For example, if nucleic acid detection methods are used, for example real time RT-PCR, OPN-c and a control (e.g., a housekeeping gene) are detected in the experimental sample. Using this information, OPN-c expression can be normalized against the expression level of a housekeeping transcript, for example by generating a ratio of OPN-c expression to control expression. The normalization can be used to correct for differences in the amount of RNA assayed and variability in the quality of the RNA used. In some examples, the method also includes detecting expression of a normalizing gene, such as a housekeeping gene. Alternatively, normalization can be based on the mean or median signal of all of the assayed genes or a large subset thereof (global normalization approach). On a gene-by-gene basis, measured normalized amount of a patient tumor mRNA can be compared to the amount found in a breast cancer tissue reference set. The number of breast cancer tissues in this reference set should be sufficiently high to ensure that different reference sets (as a whole) behave essentially the same way. Typically, the breast cancer tissue reference set consists of at least about 30 different breast cancer tissue specimens. The level measured in a particular tumor sample to be analyzed falls at some percentile within this range, which can be determined by methods well known in the art.

The higher the OPN-c:housekeeping gene expression level ratio for a particular housekeeping gene, the higher the grade of cancer in the experimental sample (e.g., grade 3), while a lower OPN-c:housekeeping gene expression level ratio for a particular housekeeping gene indicates a lower grade of cancer. One skilled in the art will appreciate that the absolute ratio for a particular OPN-c:housekeeping gene and the corresponding grade (or stage) of tumor, may vary. For example, if a control grade 3 tumor has a OPN-c:β-actin ratio of greater than 3,000, control grade 2 tumor has a OPN-c:β-actin ratio of 500 to 2,999, control grade 1 tumor has a OPN-c:β-actin ratio of 50 to 499, and the normal sample has a OPN-c:β-actin ratio of less than 50, if the experimental OPN-c:β-actin ratio obtained is 9,000 the experimental sample is concluded to be a grade 3 tumor while if the experimental OPN-c:β-actin ratio obtained is 1,000 the experimental sample is concluded to be a grade 1 tumor. On the other hand, if a different housekeeping gene is used, such as GAPDH, the range of values may differ. For example, For example, if a control grade 3 tumor has a OPN-c:GAPDH ratio greater than 10,000, control grade 2 tumor has a OPN-c:GAPDH ratio of 1000 to 9,999, control grade 1 tumor has a OPN-c:GAPDH ratio of 999 to 100, and the normal sample has a OPN-c:GAPDH ratio of less than 100, if the experimental OPN-c:GAPDH ratio obtained is 60,000 the experimental sample is concluded to be a grade 3 tumor while if the experimental OPN-c:GAPDH ratio obtained is 500 the experimental sample is concluded to be a grade 1 tumor. One skilled in the art will appreciate that the values provided are for demonstration purposes, and that absolute values or ranges of values will vary, for example depending on the method used to detect expression and the particular housekeeping gene detected.

The method can further include detecting or measuring other cancer markers in the cancer sample. For example, if the sample is a breast cancer marker, the method can include detecting or measuring one or more of estrogen receptor (ER); progesterone receptor (PR); and human epidermal growth factor receptor 2 (HER2). In some examples, ER, PR and HER2 are detected. In some examples, the read-out for ER and PR is simply positive or negative, and the read-out for HER2 is on a scale as described above for OPN-c (e.g., see Table 1). In some examples, the absence of ER (ER−) and PR (PR−) and the presence of OPN-c and HER2 in the breast cancer sample indicates that the subject has a more aggressive breast cancer (e.g., grade 2 or 3 breast cancer), while the presence of ER (ER+), PR (PR+), and lower HER2 (e.g., 0 or 1), and OPN-c (e.g., 1) in the breast cancer sample indicates that the subject has a less aggressive form of breast cancer (e.g., grade 1 breast cancer). In some examples, the presence of significant HER2 (e.g., 3 on a scale of 0 to 3) and OPN-c (e.g., 3 on a scale of 0 to 3) in the breast cancer sample indicates that the subject has a more aggressive breast cancer (e.g., grade 2 or 3 breast cancer). To assess the predictive value of several biomarkers in combination (e.g., OPN-c, ER, PR and HER2), a logistic regression modeling approach can be used, which assesses among several models the one that performs best. For the best performing model, a ROC (receiver operating characteristic) curve can be generated as a graphical plot of sensitivity/specificity as the discrimination threshold is varied.

The OPN-c, ER, PR, and HER2 molecules (as well as housekeeping genes and other cancer markers) can be detected by detecting proteins or nucleic acid molecules. For example, antibodies can be used to detect OPN-c, ER, PR, and HER2 proteins, and nucleic acid probes or primers can be used to detect OPN-c, ER, PR, and HER2 nucleic acid molecules. Methods of such detection are routine, and include immunohistological methods, Western blotting, and flow cytometry, mass spectrometry, as well as PCR and nucleic acid arrays. In some examples, the antibody or nucleic acid probe/primer includes a detectable label, such as a fluorophore, to permit detection of the antibody. In some examples, the antibody is detected with an appropriately labeled secondary antibody.

In some examples, detection of both OPN-c protein and OPN-c nucleic acid molecules in one or more biological samples obtained from the subject (such as a breast cancer tissue sample) are used to grade or stage a tumor that overexpresses OPN-c (such as DCIS).

In some examples, the method further includes selecting a treatment protocol for the subject based on the OPN-c detection. For example, if the cancer sample is highly positive for OPN-c (and in some examples negative for ER, PR, and HER2), a more aggressive therapeutic protocol can be selected and administered, as this indicates the subject has a more aggressive form of cancer (e.g., grade 3). Exemplary more aggressive therapies include a mastectomy instead of a lumpectomy, a lumpectomy combined with radiotherapy and/or chemotherapy (e.g., anti-HER2, anti-ER, and/or anti-PR therapies for example Trastuzumab (Herceptin®), bevacizumab (Avastin®), pertuzumab (OmniTarg™), ZM105180 (Zemab®), ertumaxomab (Rexonum), Arimidex® and tamoxifen) instead of lumpectomy alone, or an increase in the dose and/or number of courses of chemotherapy. Methods of administering such therapies are routine in the art and can be designed by skilled clinicians. In contrast, if the cancer sample has lower amounts of OPN-c (and in some examples negative for ER, PR, and HER2), a less aggressive therapeutic protocol can be selected and administered, as this indicates the subject has a less aggressive form of cancer (e.g., grade 1). Exemplary less aggressive therapies include a lumpectomy instead of a mastectomy, a lumpectomy alone instead of a lumpectomy combined with radiotherapy and/or chemotherapy, or a decrease in the dose and/or number of courses of chemotherapy. Methods of administering such therapies are routine in the art and can be designed by skilled clinicians.

In some examples, the diagnostic antibodies for ER, PR, HER-2 are obtained from Ventana Medical Systems (Tuscon, Ariz.). However, one skilled in the art will appreciate that other antibodies that can be used in the methods and kits provided herein are commercially available from other sources, such as: Novus Biologicals (Littleton, Colo.), Santa Cruz biotechnology, Inc. (Santa Cruz, Calif.), and Invitrogen (Carlsbad, Calif.). In some examples, the OPN-c antibody is the one described in Example 1. However, one skilled in the art will appreciate that other OPN-c antibodies that can be used in the methods and kits provided herein are commercially available from other sources, such as Gallus Immunotech, Inc. (Ontario, Canada).

Biological Samples

Exemplary samples include, without limitation, blood smears, cytocentrifuge preparations, cytology smears, core biopsies, fine-needle aspirates, and/or tissue sections (e.g., cryostat tissue sections and/or paraffin-embedded tissue sections). Methods of obtaining a biological sample from a subject are known in the art. For example, methods of obtaining breast tissue or breast cells are routine. Exemplary biological samples may be isolated from normal cells or tissues, or from neoplastic cells or tissues. Neoplasia is a biological condition in which one or more cells have undergone characteristic anaplasia with loss of differentiation, increased rate of growth, invasion of surrounding tissue, and which cells may be capable of metastasis. Exemplary neoplastic cells or tissues may be isolated from solid tumors, including breast carcinomas (e.g. lobular and duct carcinomas), adrenocortical cancer, ameloblastoma, ampullary cancer, bladder cancer, bone cancer, cervical cancer, cholangioma, colorectal cancer, endometrial cancer, esophageal cancer, gastric cancer, glioma, granular call tumor, head and neck cancer, hepatocellular cancer, hydatiform mole, lung cancer, lymphoma, melanoma, mesothelioma, myeloma, neuroblastoma, oral cancer, osteochondroma, osteosarcoma, ovarian cancer, pancreatic cancer, pilomatricoma, prostate cancer, renal cell cancer, salivary gland tumor, soft tissue tumors, Spitz naevus, squamous cell cancer, teratoid cancer, and thyroid cancer.

For example, a sample from a tumor that contains cellular material can be obtained by surgical excision of all or part of the tumor, by collecting a fine needle aspirate from the tumor, as well as other methods known in the art. If desired, the sample can be concentrated or purified before use. For example, proteins or nucleic acids can be isolated from the sample. Such methods are routine in the art. Alternatively, the sample can be used directly. In particular examples, a tissue or cell sample is applied to a substrate and analyzed to determine if it contains detectable levels of OPN-c (and in some examples also ER, PR, and HER2). A solid support useful in a disclosed method need only bear the biological sample and, optionally, but advantageously, permit the convenient detection of components (e.g., proteins and/or nucleic acid sequences) in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips. In particular examples, a breast cancer sample obtained from the subject is analyzed to determine if it contains detectable levels of OPN-c mRNA or protein.

Fixatives for mounted cell and tissue preparations are well known in the art and include, without limitation, 95% alcoholic Bouin's fixative; 95% alcohol fixative; B5 fixative, Bouin's fixative, formalin fixative, Karnovsky's fixative (glutaraldehyde), Hartman's fixative, Hollande's fixative, Orth's solution (dichromate fixative), and Zenker's fixative (see, e.g., Carson, *Histotechology: A Self-Instructional Text*, Chicago: ASCP Press, 1997).

Detection of Peptides

In particular examples, a sample obtained from the subject is analyzed to determine if it contains detectable levels of OPN-c protein. In some examples, the sample is a breast cancer sample. The sample, for example a breast cancer sample, can also be analyzed for the presence of ER, PR, and HER2 proteins.

Methods of detecting proteins are routine. In some examples, immunoassays are used to detect the presence of OPN-c protein in the sample (and in some examples additionally one or more of ER, PR, and HER2 protein). Generally, immunoassays include the use of one or more specific binding agents (such as antibodies) that can substantially only bind to the target peptide, such as OPN-c, ER, PR, and HER2. Such binding agents can include a detectable label (such as a radiolabel, fluorophore or enzyme), that permits detection of the binding to the protein. Exemplary immunoassays that can be used include, but are not limited to: Western blotting, ELISA, fluorescence microscopy, and flow cytometry. A particular immunoassay is immunohistochemistry.

In one example, the specific binding agent is an antibody, such as a polyclonal or monoclonal antibody, or fragment thereof. In some examples, the antibody is a humanized antibody. In some examples, the antibody is a chimeric antibody. If desired, the antibody can include a detectable label to permit detection and in some cases quantification of the target protein/antibody complex.

The presence of detectable signal above background or control levels indicates that the presence of a target peptide (e.g., OPN-c and in some examples additionally one or more of ER, PR, and HER2 protein) in the sample. For example, the level of OPN-c detected can be compared to a control or reference value (or range of values), such as a value that represents a level of OPN-c protein expected if a breast cancer is a grade 3, a value that represents a level of OPN-c protein expected if a breast cancer is a grade 2, a value that represents a level of OPN-c protein expected if a breast cancer is a grade 1, a value that represents a level of OPN-c protein expected if no breast cancer is present (normal tissue), or combinations thereof. Similar reference values can be used for ER, PR, and HER2 proteins. In some examples, the control is a normal (e.g., non-tumor) sample (or value expected for a normal sample).

In some examples, detection of higher levels of OPN-c indicates that subject has a grade 3 tumor, detection of intermediate levels of OPN-c indicates that subject has a grade 2 tumor, while detection of lower levels of OPN-c indicates that subject has a grade 1 tumor. In some examples, detection of higher levels of OPN-c indicates that subject has a more aggressive tumor (such as stage III or above), detection of intermediate levels of OPN-c indicates that subject has a moderately aggressive tumor (such as a stage II tumor), while detection of lower levels of OPN-c indicates that subject has a less aggressive tumor (such as a stage I or less). The amount of OPN-c detected can depend on the measurement used (e.g., see FIG. 3C). Detection of OPN-c or other cancer marker (e.g., PR, ER, HER2) can be represented as the mean cytoplasmic combined score, mean percent positive, or mean percent intensity, or other value known in the art. The value obtained for the test cancer sample can be compared to a reference value (or range of values), such as a reference value representing a value or range of values expected for grade 1, 2, or 3 breast cancer (or a particular stage of cancer). In some examples, the reference is a sample possessing a known or expected amount of OPN-c protein. For example, cell lines MCF-7 and ZR-75 are negative for OPN-c, while MDA-MB-435 and MDA-MB-231 are positive for OPN-c (all cell lines available from American Type Culture Collection). In some examples, the sample is one having a known grade 1, 2, or 3 breast cancer and a particular value or range of values for OPN-c (and in some examples also values for ER, PR, and HER2). The test value for OPN-c (and in some examples also test values for ER, PR, and HER2) can be compared to the reference value, to correlate the value to a grade of cancer. For example, if the level of OPN-c detected in the subject's sample is similar or greater than the level of OPN-c in a known grade 3 breast cancer sample or falls in the range expected for a grade 3 breast cancer, this indicates that the subject has a grade 3 breast cancer.

Detection of Nucleic Acid Molecules

In particular examples, a sample obtained from the subject is analyzed to determine if it contains detectable levels of OPN-c nucleic acid molecules (and in some examples also ER, PR, and HER2), such as a breast cancer sample, a sample adjacent to the tumor, normal breast tissue, or combinations thereof. In particular examples, OPN-c (and in some examples also ER, PR, and HER2) nucleic acid molecules (such as mRNA or cDNA) are measured.

Methods of detecting nucleic acid molecules are routine. In particular examples, a breast cancer sample obtained from the subject is analyzed to detect OPN-c nucleic acid molecules (and in some examples also ER, PR, and HER2 nucleic acid molecules), such as cDNA or mRNA. For example, assays that permit detection of nucleic acids can be used. Exemplary assays that can be used include, but are not limited to: Northern blotting, Southern blotting, PCR (such as RT-PCR or real-time RT-PCR), and DNA arrays. For example, OPN-c can be amplified from a sample using PCR, and the OPN-c amplicons detected and in some examples quantified.

In some examples, detection of higher levels of OPN-c cDNA or mRNA indicates that subject has a grade 3 tumor, detection of intermediate levels of OPN-c cDNA or mRNA indicates that subject has a grade 2 tumor, while detection of lower levels of OPN-c cDNA or mRNA indicates that subject has a grade 1 tumor. In some examples, detection of higher levels of OPN-c cDNA or mRNA indicates that subject has a more aggressive tumor (such as stage III or above), detection of intermediate levels of OPN-c cDNA or mRNA indicates that subject has a moderately aggressive tumor (such as a stage II tumor), while detection of lower levels of OPN-c cDNA or mRNA indicates that subject has a less aggressive tumor (such as a stage I or less). The amount of OPN-c cDNA or mRNA detected can depend on the measurement used.

In one example, a nucleic acid probe that hybridizes to an OPN-c nucleic acid is contacted with the breast or other cancer sample. For example, the probe can be incubated with the sample under high stringency conditions (such as when the hybridization is performed at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% Dextran sulfate, and 1-15 ng/mL probe (about $5\times10^7$ cpm/μg), while the washes are performed at about 65° C. with a wash solution containing 0.2×SSC and 0.1% sodium dodecyl sulfate), wherein the presence of higher amounts of signal indicates that the breast cancer is a grade 3 cancer and the presence of lower amounts of signal indicates that the breast cancer is a grade 1 cancer.

Real-time RT-PCR reactions can be performed using routine methods in the art. For example, a SYBR Green detection format can be used with optimized concentrations of template, primers, and $MgCl_2$. For each test sample, a no-template reaction can be included as a negative control. The reaction conditions can include 35-40 cycles of melting, a primer set specific annealing temperature, extension, and melting curve program, and finally a cooling step. Product purity, product size, and absence of primer dimers can be confirmed by DNA melting curve analysis and agarose gel electrophoresis. The threshold value for amplification can compared to a housekeeping gene and to a reference sample. The relative abundance of the RNA message is then calculated by methods known to the skilled artisan (see e.g., Pfaffl *Nucleic Acids Res.* 2001; 29:e45, herein incorporated by reference as to the method).

The value obtained (or signal detected) for the test breast cancer sample can be compared to a reference value, such as a reference value representing a value or range of values expected for grade 1, 2, or 3 breast cancer (or a particular stage of cancer). In some examples, the reference is a sample possessing a known or expected amount of OPN-c nucleic acid molecule. For example, cell lines MCF-7 and ZR-75 are negative for OPN-c, while MDA-MB-435 and MDA-MB-231 are positive for OPN-c (all cell lines available from American Type Culture Collection). In some examples, the sample is one having a known grade 1, 2, or 3 breast cancer and a particular value or range of values for OPN-c nucleic acid molecules (and in some examples also values for ER, PR, and HER2). The test value for OPN-c (and in some examples also test values for ER, PR, and HER2) can be compared to the reference value, to correlate the value to a grade of cancer. For example, if the level of OPN-c nucleic acid molecule detected in the subject's sample is similar or greater than the level of OPN-c nucleic acid molecule in a known grade 3 breast cancer sample or falls in the range expected for a grade 3 breast cancer, this indicates that the subject has a grade 3 breast cancer.

Methods of Prognosing Cancer

Methods are provided herein for prognosing a cancer by examining OPN-c levels in a tumor sample obtained from a subject. OPN-c can be detected as described above, wherein the presence of significant amounts of detectable OPN-c in the cancer sample (e.g., top ⅓ intensity or top ⅔ intensity) indicates that the subject has a worse prognosis while the presence of lower amounts of detectable OPN-c (e.g., lower ⅓ intensity) in the cancer sample indicates that the subject has a better prognosis. Detection of OPN-c in a tumor sample can be used to prognose any OPN-expressing tumor, such as adrenocortical cancer, ameloblastoma, ampullary cancer, bladder cancer, bone cancer, breast cancer, cervical cancer, cholangioma, colorectal cancer, endometrial cancer, esophageal cancer, gastric cancer, glioma, granular call tumor, head and neck cancer, hepatocellular cancer, hydatiform mole, lung cancer, lymphoma, melanoma, mesothelioma, myeloma, neuroblastoma, oral cancer, osteochondroma, osteosarcoma, ovarian cancer, pancreatic cancer, pilomatricoma, prostate cancer, renal cell cancer, salivary gland tumor, soft tissue tumors, Spitz naevus, squamous cell cancer, teratoid cancer, and thyroid cancer.

Prognostic methods can be used to predict likely tumor progression, survival time, likely worsening of the condition, and the like, for example the prognosis in the absence of therapy (e.g., chemotherapy or radiation therapy). For example, the methods can be used to determine whether a tumor may be less aggressive (e.g., less rapidly growing, and/or less likely to metastasize) or more aggressive (e.g., rapidly growing, and/or more likely to metastasize), for example independent of therapy. A less-aggressive tumor can be characterized by any parameters known in the art, including, for instance, decreased growth rate (e.g., increased rate of apoptosis and/or decreased rate of cell division), decreased rate of metastasis, and/or increased sensitivity to chemotherapy. A more aggressive tumor can be characterized by any parameters known in the art, including, for instance, increased growth rate (e.g., decreased rate of apoptosis and/or increased rate of cell division), increased rate of metastasis, and/or decreased sensitivity to chemotherapy. In some examples, prognosis for a subject can be characterized by actual survival after initial diagnosis (such as 6-month survival, 1-year survival, 2-year survival, or 5-year survival), and/or actual survival relative to the average survival for similarly situated patients. A better prognosis entails, e.g., survival of a patient for more than 1 year after initial diagnosis (such as more than 2 years or more than 5 years), or survival of a patient for more than 6 months longer (e.g., more than 1 year longer, more than 2 years longer, more than 5 years longer) than the average survival for similarly situated. A worse prognosis entails, e.g., survival of a patient for less than 5 years after initial diagnosis (such as less than 2 years or less than 1 years), or survival of patient less than the average survival for similarly situated patients (such as, about 3 months less than average survive, about 6 months less than average survive, or about 1 year less than average survival).

As described above, in some examples, the amount of OPN-c is quantified or scaled, wherein higher levels of OPN-c indicate a more aggressive cancer and a worse prognosis, and lower levels of OPN-c indicate a less aggressive cancer and better prognosis. For example, if the typical 1+ to 3+ scale is to represent the intensity as described above, if a level of "1" is detected for OPN-c, this indicates that the subject has a less aggressive cancer (e.g., decreased likelihood of death within 5 years of diagnosis or decreased likelihood of metastasis), while detection of a level "3" for OPN-c indicates that the subject has an aggressive cancer (e.g., increased likelihood of death within 5 years of diagnosis or increased likelihood of metastasis). In other examples, the mean combined score method is used as described above (where scores range from 0 to 300). For example, the resulting value from the experimental sample in the range of 0 to 300 can be compared to control samples having known prognosis and values on the 0 to 300 sale, or can be compared to expected values on the 0 to 300 scale for each prognosis. For example if a control poor prognosis (e.g., 5 year survival rate of less than 5%) has a range of 250 to 300, and a control good prognosis (e.g., 5 year survival rate of greater than 95%) has a range of 0 to 49, if the experimental value obtained is 275 the experimental sample is concluded to have a poor prognosis while if the experimental value obtained is 20 the experimental sample is concluded to have a good prognosis. One skilled in the art will appreciate that the values provided above are for demonstration purposes, and that absolute values or ranges of values will vary, for example depending on the method used to detect expression.

In other examples, OPN-c nucleic acid levels present in a subject sample are normalized as described above (see for example U.S. Pat. Nos. 7,056,674 and 7,081,340; herein incorporated by reference). In particular examples, the higher the ratio for a particular housekeeping gene, the worse the prognosis, while a lower ratio for a particular housekeeping gene indicates a better prognosis.

Kits

The present disclosure provides kits that can be used to grade, stage, and prognose abreast or other OPN-expressing cancer, for example to determine if a cancer is more or less aggressive, determine the likelihood that a cancer will metastasize, and predicting the survival time of a subject with cancer. Generally cancer grading is performed on a scale of 1 to 3, with 1 being less aggressive and 3 being the most aggressive.

In particular examples, the kit includes or consists of an antibody that specifically binds estrogen receptor (ER); an antibody that specifically binds progesterone receptor (PR); an antibody that specifically binds HER2; and an antibody that specifically binds OPN-c. In some examples, the kit does not include a PR antibody. In some examples, the kit includes or consists of a nucleic acid probe or primer specific for an ER nucleic acid sequence; a nucleic acid probe or primer specific for a PR nucleic acid sequence; nucleic acid probe or primer specific for a HER2 nucleic acid sequence 2; and nucleic acid probe or primer specific for an OPN-c nucleic acid sequence. In particular examples, the kit does not include a PR nucleic acid probe or primer. In some examples, the antibody or nucleic acid probe or primer is labeled (for example, with a fluorescent, radioactive, or an enzymatic label).

In some embodiments, the antibodies, probes, or primers are provided suspended in an aqueous solution or as a freeze-dried or lyophilized powder, for instance. The container(s) in which the antibodies, probes, or primers are supplied can be any conventional container that is capable of holding the supplied form, for instance, microfuge tubes, ampoules, or bottles. The amount of antibodies, probes, or primers supplied can be any appropriate amount, such as from about 1 to about 5 µg/ml.

In other embodiments, control slides upon which are mounted one or more tissue or cell preparations (e.g., xenografts, cell pellets, or clotted cells) that may serve as positive and/or negative controls for OPN-c, ER, PR, and/or HER2 expression may be provided in an appropriate and separate container.

The kits can include antibodies or nucleic acid molecules specific for one or more housekeeping molecules, such as one or more of GAPDH (glyceraldehyde 3-phosphate dehydrogenase), SDHA (succinate dehydrogenase), HPRT1 (hypoxanthine phosphoribosyl transferase 1), HBS1L (HBS1-like protein), β-actin, and AHSP (alpha haemoglobin stabilizing protein).

The kit can also include one or more control samples, such as positive or negative control samples. For example, a controls sample can be a normal breast or breast cancer sample with known relative amounts of ER, PR, HER2 and OPN-c. In a particular example, the control sample is a xenograft control.

One skilled in the art will appreciate that the kits can include other agents to facilitate the particular application for which the kit is designed. For example, the kit can additionally contain means of detecting a label (such as enzyme substrates for enzymatic labels, filter sets to detect fluorescent labels, appropriate secondary labels such as a secondary antibody, or the like), as well as buffers and other reagents routinely used for the practice of a particular diagnostic method.

Example 1

Materials and Methods

This example describes the materials and methods used to obtain the results described in Examples 2-5. Although particular exemplary methods and materials are described, one skilled in the art will appreciate that variations can be made. For example, different antibodies can be used.

Human Breast Cancer RNA:

Specimens of human breast tumors, non-transformed surrounding tissue, as well as healthy breast tissue (obtained from reduction mammoplasties) were provided by the tissue procurement facility of the University of Cincinnati Medical Center/Children's Hospital. Samples were obtained from 20 invasive ductal carcinomas at grades II-III. The average patient age was 55 years, ranging from 35 to 84 years. The tumor stages ranged from T1 to T4 and from N0 to N4, the status of metastases was unknown in all cases. Eleven samples of tumor-surrounding tissue came from patients with the mean age of 61 years, ranging from 46 to 84 years. Normal tissues were obtained from 22 reduction mammoplasties. The patient age ranged from 21 to 57, with an average of 36.5 years. Total RNA was extracted from specimens using TRIZOL® Reagent (Invitrogen). Total RNA was used for cDNA synthesis by reverse transcription using Superscript II (Invitrogen) according to the manufacturer's protocol in a total volume of 20 µl.

PCR Amplification:

All PCR reactions were performed on a Cepheid (Sunnyvale, Calif.) Smart Cycler using SYBR Green detection format. 0.5 µl of cDNA was added to each PCR reaction in a total volume of 25 µl using the standard Invitrogen PCR buffer system with optimized concentrations of MgCl$_2$. For each experiment a no-template reaction was included as a negative control. The conditions for PCR were 94° C. denaturation for 120 s followed by 35-40 cycles of: 94° C. melting for 15 s, a primer set specific annealing temperature (Table 2), extension at 72° C. and melting curve program (60-95° C. with a heating rate of 0.2° C. per second and a continuous fluorescence measurement), and finally a cooling step to 4° C. Product purity, product size, and absence of primer dimers were confirmed by DNA melting curve analysis and agarose gel electrophoresis. Melt curves yielded a single sharp peak for all template reactions, and a minimal melt peak (resulting from primer dimers) or no melt peaks for the no-template control reactions.

conjugated goat anti-chicken IgY secondary antibody (Jackson ImmunoResearch Laboratories, West Grove, Pa.) diluted to 1:80 in Ventana Antibody diluent (devoid of casein and azide), was applied for 16 minutes at room temperature. Antibody binding was detected using the ChromoMap™ DAB detection kit (Ventana Medical Systems). Rabbit monoclonal antibodies to human estrogen receptor (ER, clone SP1), progesterone receptor (PR, clone 1E2), and to HER2 (clone 4B5) from VMSI were also used to stain the breast carcinoma array, and were detected using the Ultra-View™ DAB kit (VMSI). The primary antibody was applied for 16 minutes at 37° C. and the HRP-conjugated anti-rabbit secondary antibody was applied for 8 minutes at 37° C. All

TABLE 2

Primer pairs for real-time RT-PCR.

| Target sequence | Primer | Sequence (SEQ ID NO:) | | Product size (bp) | [Mg$^{2+}$] (mM) | Annealing (° C.) |
|---|---|---|---|---|---|---|
| OPN-a | forward | 5'-ATCTCCTAGCCCCACAGAAT-3' | (1) | 208 | 2.5 | 58 |
| | reverse | 5'-CATCAGACTGGTGAGAATCATC-3' | (2) | | | |
| OPN-b | forward | 5'-ATCTCCTAGCCCCAGAGAC-3' | (3) | 209 | 2.5 | 62 |
| | reverse | 5'-AAAATCAGTGACCAGTTCATCAG-3' | (4) | | | |
| OPN-c | forward | 5'-TGAGGAAAAGCAGAATGCTG-3' | (5) | 155 | 3.0 | 62 |
| | reverse | 5'-GTCAATGGAGTCCTGGCTGT-3' | (6) | | | |
| β-Actin | forward | 5'-GGCGGCACCACCATGTACCCT-3' | (7) | 200 | 2.0 | 65 |
| | reverse | 5'-AGGGGCCGGACTCGTCATACT-3' | (8) | | | |
| Ck-19 | forward | 5'-CCCGCGACTACAGCCACTA-3' | (9) | 163 | 2.0 | 60 |
| | reverse | 5'-CTCATGCGCAGAGCCTGTT-3' | (10) | | | |
| aP2 | forward | 5'-TCAGTGTGAATGGGGATGTG-3' | (11) | 249 | 1.6 | 58 |
| | reverse | 5'-GTGGAAGTGACGCCTTTCAT-3' | (12) | | | |

Shown are the primer sequences and the sizes of the resulting PCR products. The magnesium concentrations and annealing temperatures are indicated as optimized in preliminary experiments. The primer sets for osteopontin (OPN) were designed to distinguish the splice variants. The primer sets for CK-19 (Benoy et al., Brit. J. Canc. 91:1813-20, 2004), β-actin and aP-2 covered two different exons to avoid amplification of any contaminating genomic DNA. Amplification efficiencies were determined for each given primer set by cDNA dose-response curve analysis.

For conventional RT-PCR, the osteopontin splice variants were amplified with specific primer pairs [14, herein incorporated by reference as to the primers]. The amplification of GAPDH with primers 5'-TGAAGGTCGGAGTCAACG-GATTTGGT-3' (forward; SEQ ID NO: 13) and 5'-CAT-GTGGGCCATGAGGTCCACCAC-3' (reverse; SEQ ID NO: 14) served as a control for equal loading and integrity of the cDNA. All PCR products were analyzed by Tris-acetate EDTA agarose (2.5% w/v) gel electrophoresis.

Immunohistochemistry:

A normal breast multi-array (Cybrdi, Fredrick, Md.) containing 69 normal cores (plus three infiltrating ductal carcinomas as references) and a breast carcinoma multi-array containing 56 cancer cores confirmed by the examining pathologist (7 cores were diagnosed not to contain carcinoma and were therefore excluded), were stained for OPN-c. The carcinoma array included intraductal carcinomas, infiltrating ductal carcinomas, infiltrating lobular carcinomas, papillary adenocarcinomas, mucinous adenocarcinomas, and Paget's disease.

The immunohistochemistry analyses were conducted on the automated Discovery™ or Benchmark™ staining platform (Ventana Medical Systems, Tucson, Ariz.). Antigen retrieval for osteopontin-c was not required. The slides were incubated with an affinity-purified anti-OPN-c chicken IgY (produced by Gallus Immunotech), at 1:160 dilution for 32 minutes at room temperature. The secondary antibody, HRPslides were counterstained with Hematoxylin II (VMSI) for 8 minutes followed by Bluing Reagent (VMSI) for 4 minutes at room temperature.

The tissue arrays were assessed by a board-certified pathologist. The cytoplasm was scored using a typical 1+ to 3+ scale to represent the intensity, with 3 being assigned to very intensely staining samples, 1 to weakly staining samples, and 0 to negatively staining samples. Combined pathology scores were calculated from mean intensity (ranging from 1 to 3) multiplied by mean percent (ranging from 0 to 100) of tissue stained for the individual samples of the breast arrays. The highest possible score is 300. To assign a tumor grade, the modified Scarff-Bloom-Richardson (SBR) system [15] was used, which considers nuclear grade, tubule formation, and mitotic rate. The combination of scores for these factors was applied to assign a grade of 1, 2, or 3.

DNA Constructs and Transfection:

The constructs for expression of the human osteopontin splice variants were obtained by reverse transcription-PCR from the malignant breast tumor cell line MDA-MB-435. The coding sequence of osteopontin was amplified with the primers 5'-CAA ACG CCG ACC AAG GGA AAA C-3' (SEQ ID NO: 15) and 5'-CTT CTT TCT CAG TTT ATT GGT-3' (SEQ ID NO: 16). The amplified product was TA cloned, excised with XhoI and NheI, and was subcloned into the vector pCR3.1 (Invitrogen Carlsbad, Calif.). Genes cloned into this vector are expressed under the control of the CMV promoter. Sequence fidelity and accurate reading frame were verified by DNA sequencing analysis. MCF-7 cells were transfected by the Fugene method and stable clones were selected in G418.

Immunoblot Assay:

For the analysis of secreted osteopontin, serum-free cell culture supernatant was collected from each transfectant. 40 µl of supernatant per sample were electrophoresed on 10% SDS-polyacrylamide mini-gels with non-reducing sample buffer. For the analysis of intracellular osteopontin, the cells were lysed in RIPA buffer (50 mM Tris-HCl pH 7.5, 150 mM NaCl, 1% NP-40, 0.5% Na-deoxycholate, 0.1% sodium dodecyl sulfate). Cell lysates at equal amounts of protein (20 µg/lane) were electrophoresed on reducing 10% SDS-polyacrylamide gels. The separated proteins were transferred to PVDF membranes and probed with antibody O-17 (Assay Designs Inc.) to osteopontin.

Example 2

Osteopontin-c RNA is Expressed in Breast Cancer but not in Normal Breast Tissue

This example describes results of measuring osteopontin gene expression in breast cancer specimens, tumor-surrounding tissues, and normal samples by real-time RT-PCR using splice variant specific primers and the amplification of β-actin as a control for abundance.

Because breasts contain various amounts of fat and the source of osteopontin are selectively the epithelial cells, the levels of cytokeratin-19 (CK-19, epithelial marker) and aP2 (adipocyte marker) were measured and the results adjusted to account for the fraction of epithelial cells. As shown in FIGS. 1A and 1B, OPN-c was detected in 16 of 20 tumors and the RNA levels had a relative abundance comparable to the full length form osteopontin-a. In contrast, there was no detectable OPN-c in any of the normal tissues examined. Seven of eleven tumor-surrounding normal tissues were devoid of OPN-c. It is not known whether the four normal specimens that showed OPN-c expression had cryptic tumor cell infiltration or a reaction to the tumor, such as inflammation. All four were grade 3 tumors without Paget disease, but their tumor stages varied.

The expression levels of OPN-a varied in 21 specimens of normal breasts, with only four samples lacking detectable levels (FIGS. 1A and 1B). This may reflect the production of unspliced osteopontin, which is physiologically secreted in milk, by breast cells depending on the stages of the estrous cycle. The splice variant OPN-b was present at low levels in 18 of 20 cancers, in eight of eleven tumor surrounding tissues, and in six of 22 normal breasts (FIGS. 1A and 1B).

Statistical evaluations were performed on the data from the real time RT-PCR measurements. According to the analysis of variance (ANOVA) on ranks, the levels of osteopontin-c in the tumors are different ($p<0.05$) from the levels of OPN-c in the normal samples. The tumor-surrounding tissues have intermediate values and are not different from either the tumors or the normal samples. Analogous results were obtained for OPN-b. For osteopontin-a, no differences were detected among the three groups of samples. The proportion of positives for OPN-c RNA were compared among the groups by the chi-square test ($\chi^2=13.33$, $p<0.001$), and the proportion of positives differed between normal breasts and breast cancers ($p<0.0007$ by Fisher's exact test), while it was not significantly different between tumors and surrounding normal tissues ($p=0.16$ by Fisher's exact test).

Every PCR run included a negative control without a template and a known cDNA reference sample as a positive control. For the osteopontin splice variants and β-actin, the positive control was the MDA-MB-435 breast cancer cell line that produces large amounts of RNA for all three osteopontin forms. The positive control for CK-19 was the breast tumor cell line MCF-7, while a fatty breast specimen provided the reference for aP2. OPN-a and β-actin levels were highly reproducible in these samples. The range encountered for the other amplicons also indicated good reproducibility, but was wider. The exact quantification of low abundance RNA messages is inherently more subject to fluctuations than higher abundance messages (FIG. 1C). In sum, with the inclusion of suitable controls, the accuracy of these measurements will allow diagnostic or prognostic decisions to be based on them.

Example 3

The Levels of OPN-c Correlate with Tumor Grade in Histology

An IgY antibody was raised to the splice junction of OPN-c. The antibody selectively recognized OPN-c, but not OPN-a on Western blots (FIG. 2A). In a solid-phase ELISA, the antibody reacted strongly with GST-OPNc, but only weakly with GST-OPNa, whereas the pan-osteopontin antibody O-17 (Assay Designs Inc.) showed very strong reactivity with both GST-OPN forms.

Figure 2B:
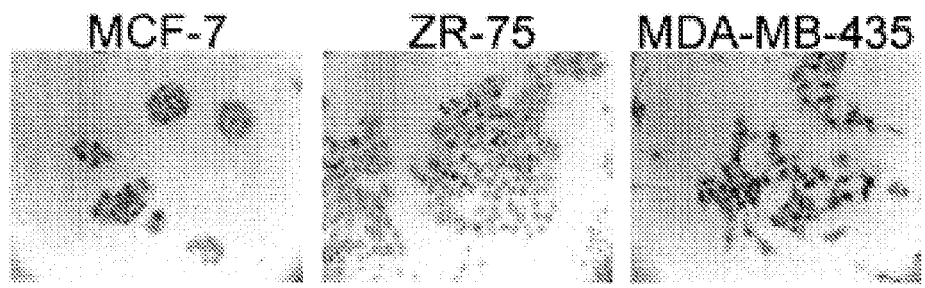
Figure 2C:
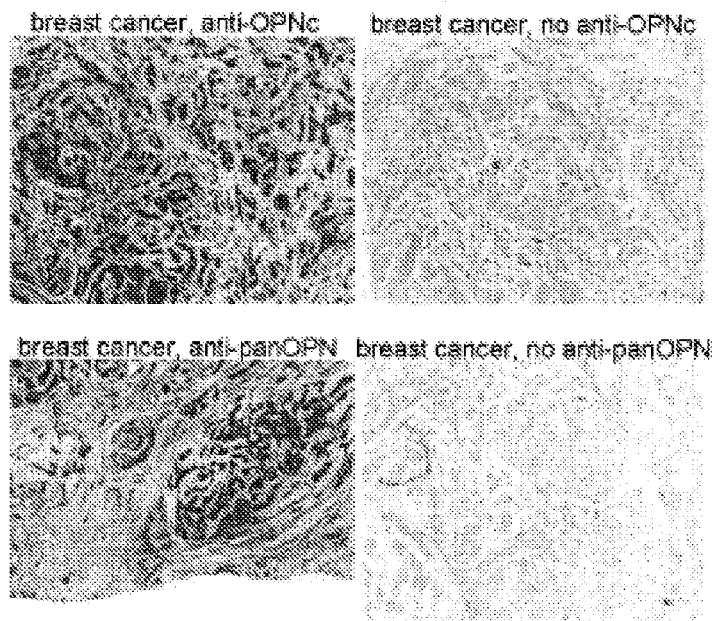

Immunocytochemistry was performed on cell lines with previously confirmed distinct osteopontin expression levels [14]. Consistently, strong cytoplasmic staining was seen in MDA-MB-435 cells, but not in MCF-7 cells or ZR-75 cells (FIG. 2B). Staining of breast cancer tissue with the anti-hOPNc antibody was compared to the anti-pan-osteopontin antibody O-17. The cancer was strongly positive for total osteopontin and for OPN-c. In the absence of the respective primary antibodies, no staining was observed (FIG. 2C).

Figure 3A:
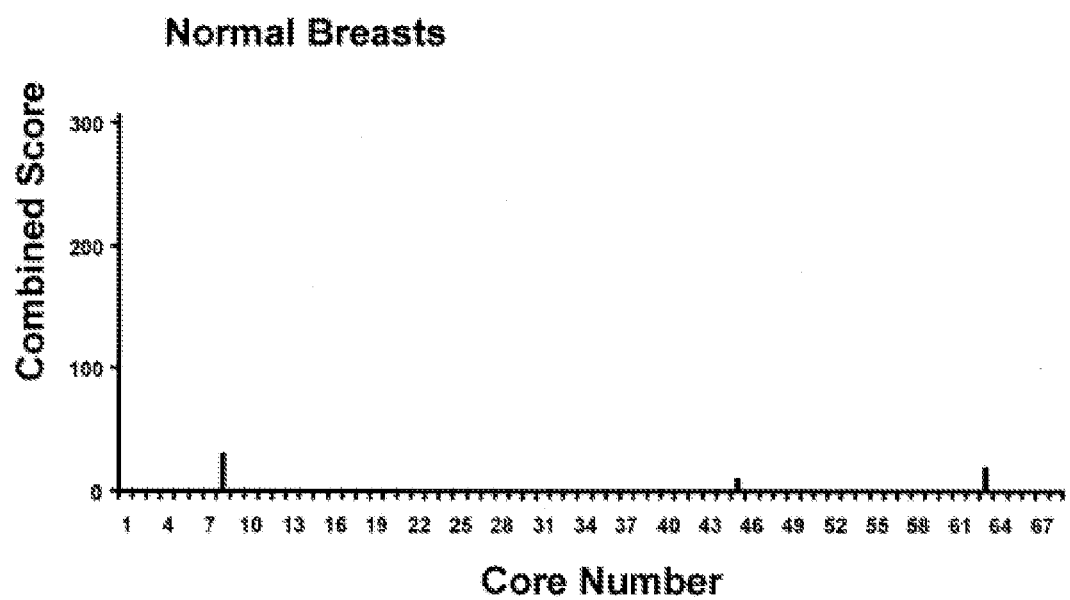
FIGS. 3A-C: Expression of osteopontin-c protein in breast tissue. Tissue arrays were stained by immunohistochemistry and scored by a board-certified pathologist. A) Combined pathology scores (mean intensity multiplied by mean percent of tissue stained) for the individual samples of the normal breast array (top) and the breast carcinoma array (bottom). Note that the highest positively scoring core, number 7, in the normal breast array was judged to be possibly cancerous. B) Representative images (taken at 40× magnification) of the immunohistochemical staining for OPN-c. Increasing grades are shown for intraductal carcinoma, infiltrating lobular carcinoma, and papillary adenocarcinoma. The insert depicts a normal breast tissue specimen as a reference. The slides are counterstained with Hematoxylin II and Bluing Reagent (Ventana Medical Systems Inc.). C) Pathology scores for tumors of increasing grade (left panel) or of tumors versus normal breasts (right panel). Shown are the mean cytoplasmic combined score (top row), the mean percent positive cells (middle row), and the mean cytoplasmic intensity (bottom row). The error bars represent SEM.
Figure 3A:
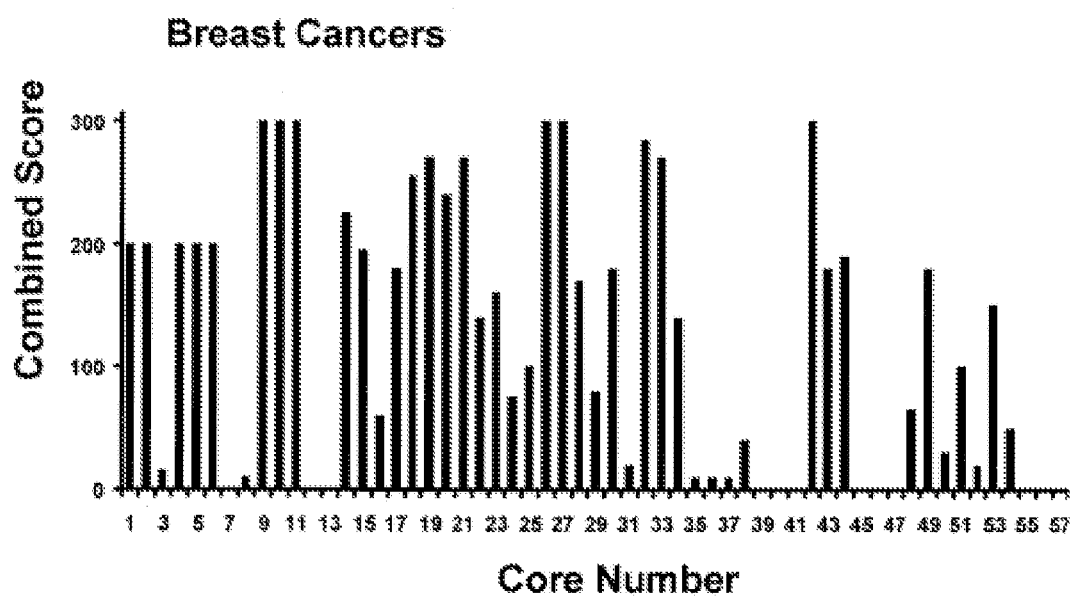
Figure 3B:
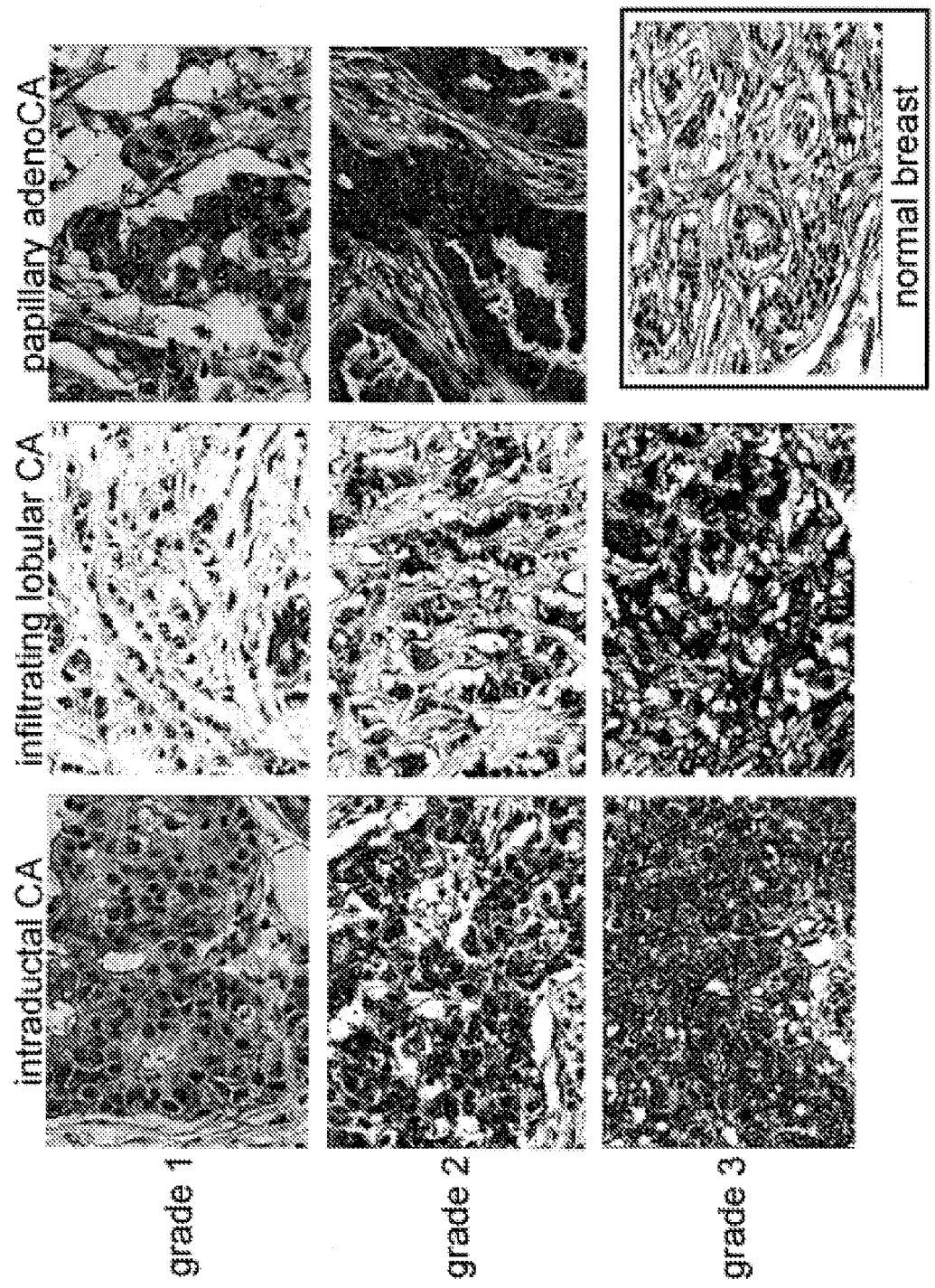
Figure 3C:
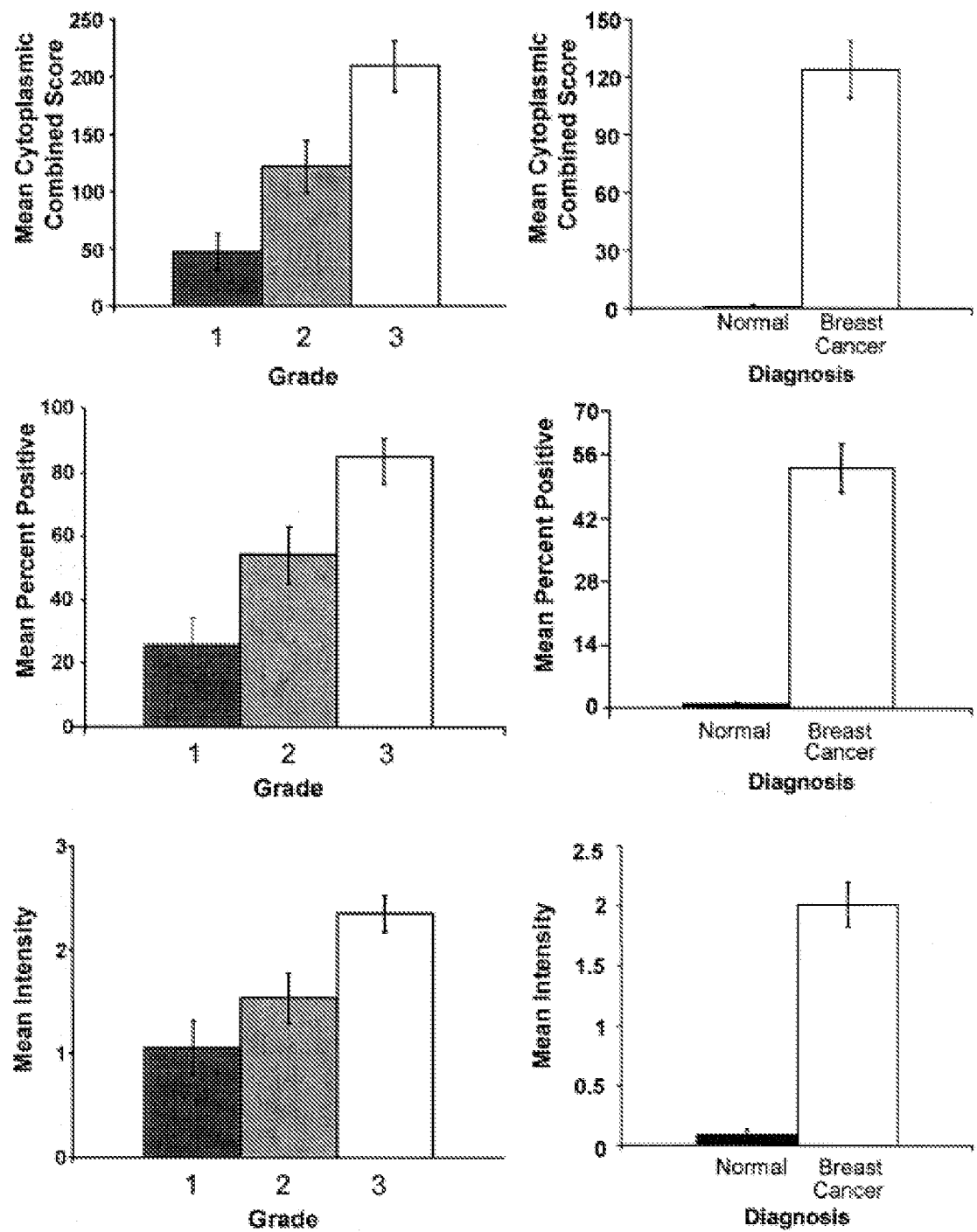

The generated OPN-C antibody was used to analyze breast tissue arrays by immunohistochemistry. As shown in FIG. 3A, three of 69 normal breasts had low positive staining, while all the others were negative. Among the breast carcinomas, 43 of 56 cores (77%) stained positive for OPN-c while 13 tissue samples were negative. When analyzed for its correlation with tumor grade, OPN-c staining increased from grade 1 to grade 3 (FIG. 3B), regardless of whether mean intensity, mean percent positive, or the mean cytoplasmic combined score was used as a mode of assessment (FIG. 3C).

Example 4

OPN-c is a More Sensitive Marker for Breast Cancer than ER, PR, or HER2

The growth factor receptors estrogen receptor (ER), progesterone receptor (PR) and HER2 may be up-regulated in breast cancer and are used in diagnosis to facilitate therapy decisions. Therefore OPN-c expression was compared to these markers.

Figure 4A:
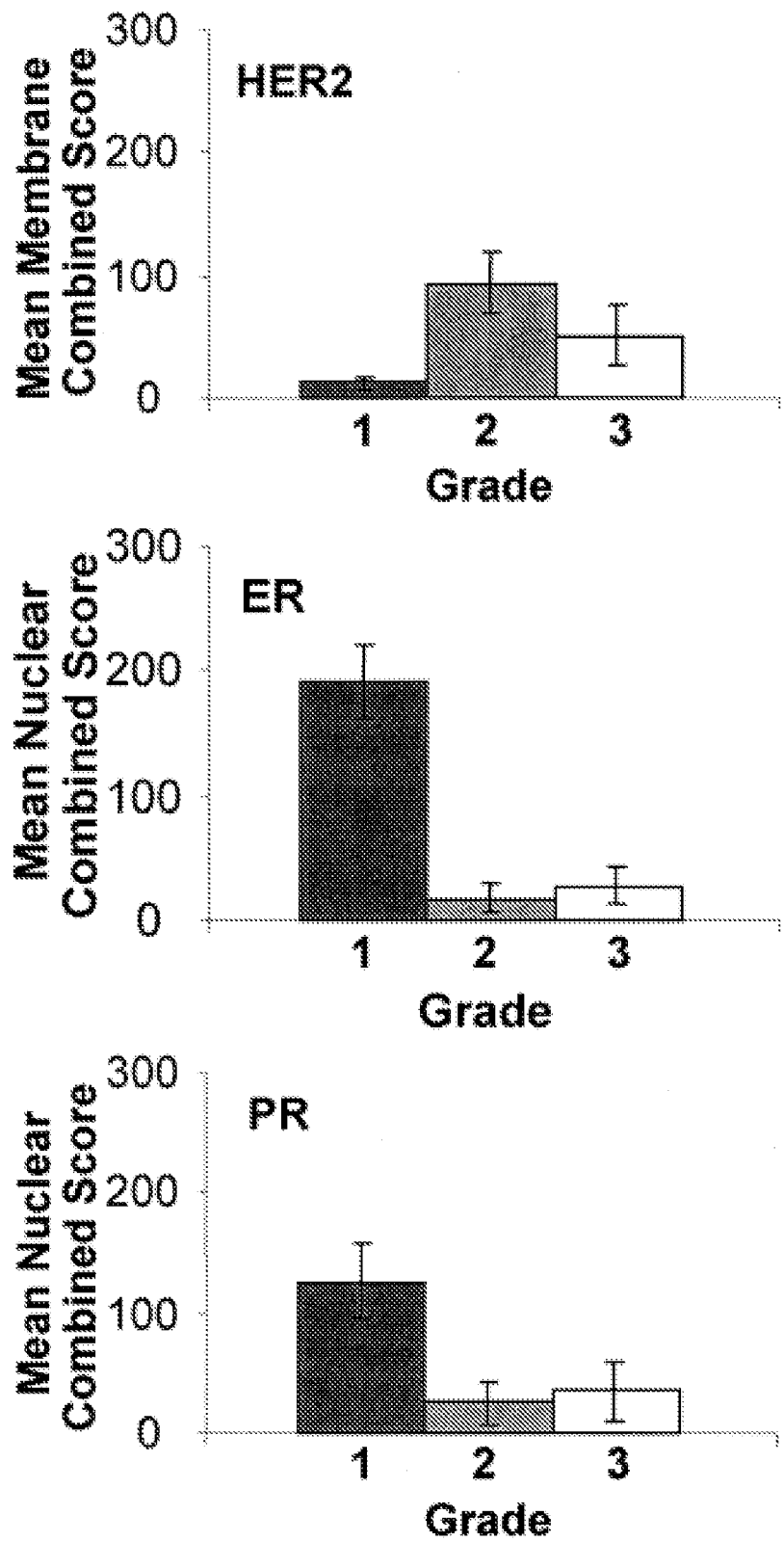
FIGS. 4A-C: OPN-c is a more sensitive marker for breast cancer than ER, PR, or HER2. A) Pathology scores for tumors of increasing grade. Shown are the mean combined scores for ER (top), PR (middle) and HER2 (bottom). The error bars represent SEM. B) Spearman's rank correlation coefficients (SRCC) and associated confidence parameters for the correlation of breast carcinoma staining for OPN-c with the staining observed for ER, PR and HER2 by immunohistochemistry. The scatter plots show the combined mean scores for osteopontin-c versus ER, PR or HER2. C) Threshold probabilities for the best performing logistic regression model for predicting breast cancer grades 2 or 3 with a combination of OPN-c, ER, and HER2.

Of the 56 cores, 28 were positive and 28 were negative for ER, 19 were positive and 37 were negative for PR, and there were 14 HER2 positive and 42 HER2 negative cores. Tumors with high expression of HER2 were low or negative for ER and PR. Conversely, ER and PR staining were high in breast cancer specimens with low or absent HER2. Whereas increasing tumor grade was associated with an increase in positivity for OPN-c staining according to mean combined score, mean percent positive, and mean intensity (compare FIGS. 3B and 3C), ER and PR were substantially reduced in higher grade tumors. HER2 was slightly higher in grades 2 and 3 than in grade 1 (FIG. 4A).

Figure 4B:
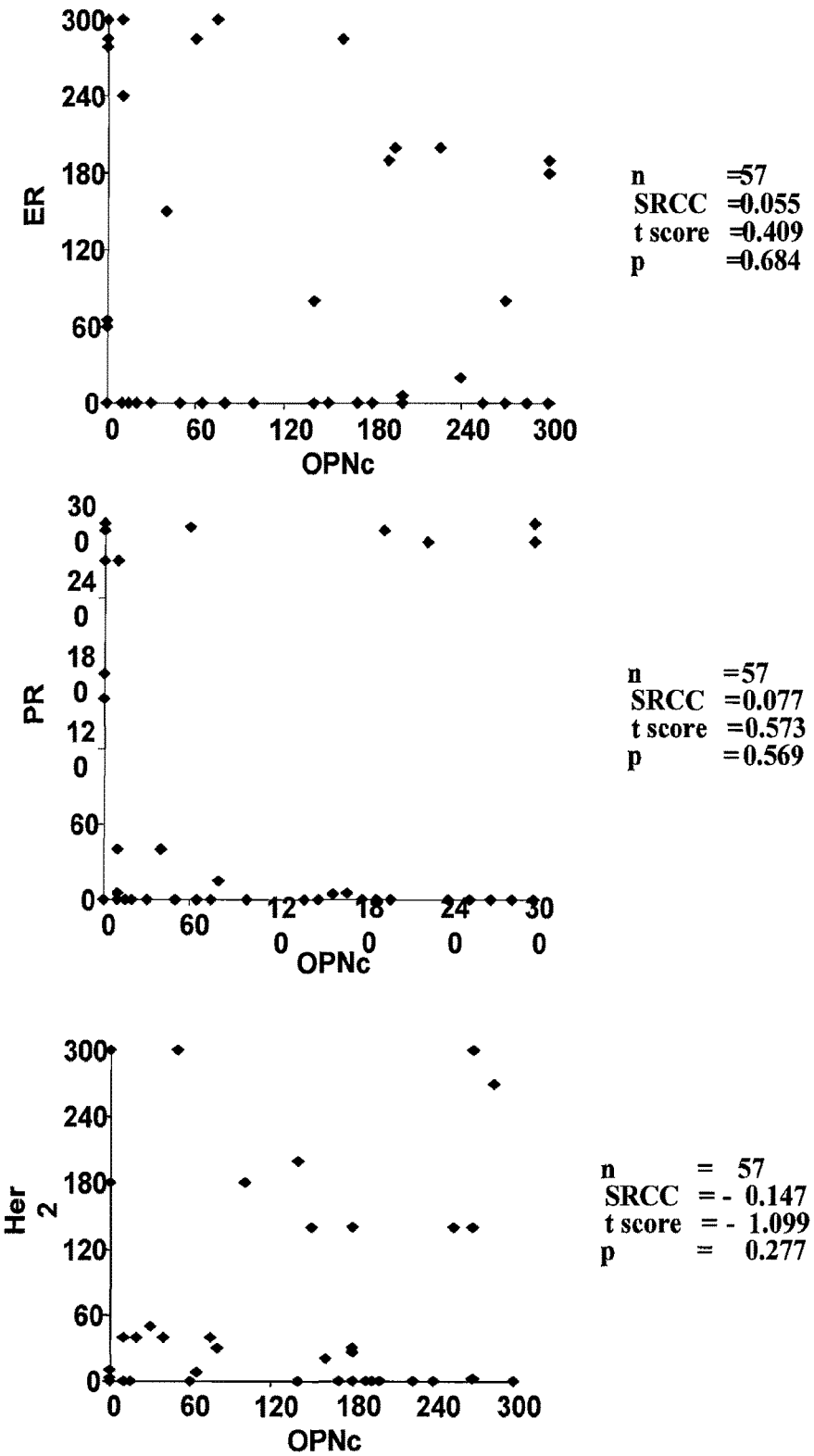

To determine whether the cytoplasmic OPN-c staining of breast carcinomas was correlated with the membrane staining of HER2 or the nuclear staining of ER and PR, the mean combined scores were compared according to Spearman's rank correlation coefficient (SRCC) [16]. There was no significant correlation between OPN-c and any of these three breast markers. Only a tentative correlation according to SRCC was found with HER2 (FIG. 4B). As a metastasis gene, OPN-c is a marker for different characteristics of breast cancer than these growth factor receptors.

Figure 4C:
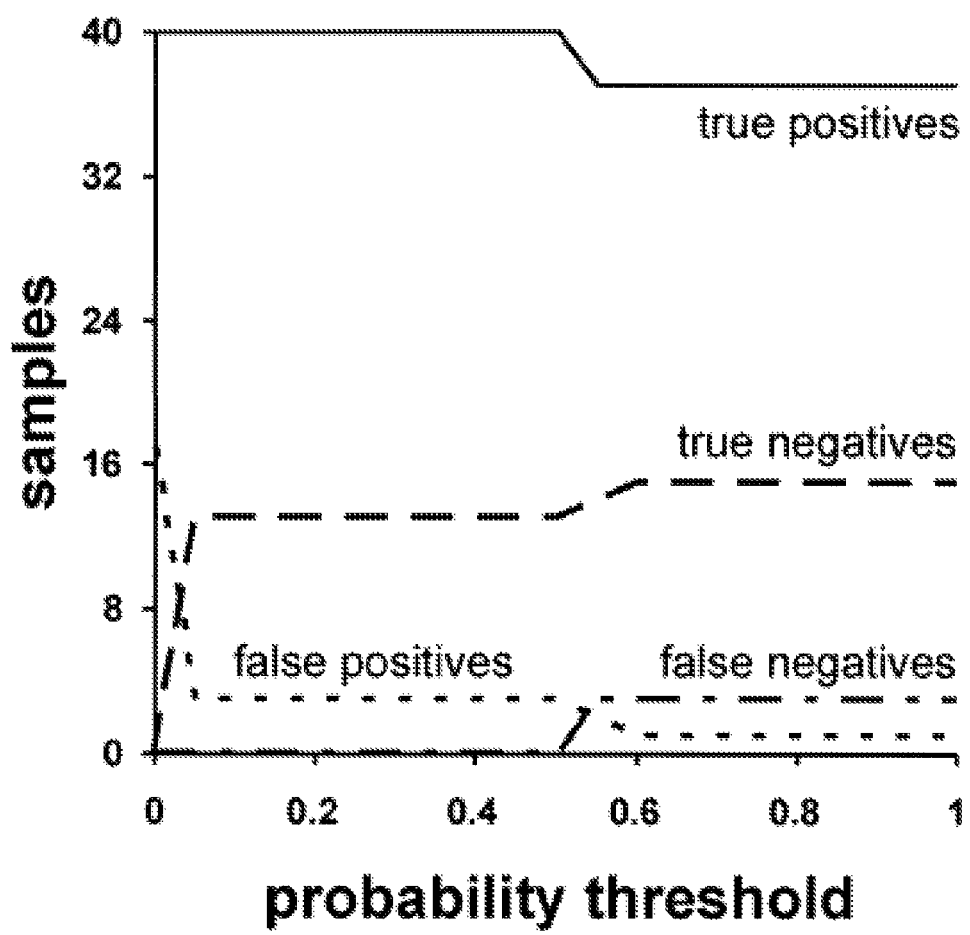

It was then determined whether OPN-c has diagnostic value in conjunction with ER, PR and HER2. Applying a logistic regression modeling approach [17, 18], OPN-c was the best single predictor of a grade 3 cancer (ROC score 0.809; ROC score for ER 0.575, for PR 0.570, for HER2 0.551). Furthermore, the combination of OPN-c, ER and HER2 can diagnose grade 2-3 tumors with high reliability (ROC score 0.979) (FIG. 4C). In this model, high OPN-c and HER2 scores correspond to a higher likelihood of grade 2-3, and higher ER corresponds to a lower probability of grade 2-3. PR had poor predictive value.

Triple-negative breast cancer (missing ER, PR, and HER2) lacks the benefit of a specific therapy and is associated with a difficult risk assessment [19]. For all grades of breast cancer, 14% of the tissue cores that were positive for OPN-c were not stained by ER, PR, or HER2. Selectively for the highest grade of cancer (grade 3), approximately 35% of the cases that were stained by anti-OPN-c were negative for all of the 3 other breast cancer markers tested (Table 3). Hence, OPN-c detects a larger fraction of breast cancers than do ER, PR or HER2. It can therefore indicate transformation in cases where the other three markers fail.

Example 5

OPN-c Expression in Other Cancers

Beside breast cancer, osteopontin has been associated with the progression of other malignancies, including colon cancer, ovarian cancer, hepatocellular carcinoma, and glioblastoma. A limited number of colon tumors (n=6), their surrounding tissues (n=4), and colitis specimens (n=3) were obtained and expression levels of osteopontin splice variants analyzed using real-time RT-PCR.

While the sample numbers are still small, they indicate that a proportion of colorectal carcinomas produce spliced osteopontin (Table 4). In fact, while OPN-a was very low in the tumors (m=0.024, range 0-0.088) and moderate in the adjacent tissues (m=0.258, range 0-0.543), the RNA message for OPN-c was expressed at very high levels in the tumors (m=0.474, range 0-1.5) and at moderate levels in the adjacent tissues (m=0.255, range 0-1.020). In the colitis samples, the expression of OPN-a was low, while OPN-b and OPN-c were barely detectable.

In contrast to breast tissues, where normal specimens are accessible from reduction mammoplasties, this type of source is not available for colon. The comparison to colitis samples is somewhat compromised because several cell types of the immune system can produce osteopontin, although physiologic splicing of the osteopontin message has not yet been described. These results indicate that OPN-c is a marker of invasiveness not only for breast cancers, but also for other malignancies. Therefore, the methods and kits provided herein can be used not only for breast cancers, but other cancers as well (e.g., those that express OPN such as adrenocortical cancer, ameloblastoma, ampullary cancer, bladder cancer, bone cancer, breast cancer, cervical cancer, cholangioma, colorectal cancer, endometrial cancer, esophageal cancer, gastric cancer, glioma, granular call tumor, head and neck cancer, hepatocellular cancer, hydatiform mole, lung cancer, lymphoma, melanoma, mesothelioma, myeloma, neuroblastoma, oral cancer, osteochondroma, osteosarcoma, ovarian cancer, pancreatic cancer, pilomatricoma, prostate cancer, renal cell cancer, salivary gland tumor, soft tissue tumors, Spitz naevus, squamous cell cancer, teratoid cancer, and thyroid cancer). OPN-c can be evaluated in such tissues using the methods provided herein.

TABLE 3

Histochemical staining for OPN-c, ER, PR, and HER2.

| tumor grade | n | OPNc+ 3 receptors negative | OPNc+, 1 receptor positive | OPNc+, 2 receptors positive | OPNc+, 3 receptors positive | all negative | OPNc−, 1 receptor positive | OPNc−, 2 receptors positive | OPNc−, 3 receptors positive |
|---|---|---|---|---|---|---|---|---|---|
| 1 | 16 | 0% | 12.5% | 43.8% | 0% | 6.3% | 6.3% | 25.0% | 6.3% |
| 2 | 23 | 8.7% | 56.5% | 8.7% | 0% | 13.0% | 13.0% | 0% | 0% |
| 3 | 17 | 35.3% | 41.2% | 23.5% | 0% | 0% | 0% | 0% | 0% |
| all grades | 56 | 14.3% | 39.3% | 23.2% | 0% | 7.1% | 7.1% | 7.1% | 1.8% |

The comparison of percentages of samples staining positively for osteopontin-c versus all three growth factor receptors in breast carcinoma tissue array cores indicates that OPN-c is a more sensitive marker. It also detects a fraction of triple negative breast cancers. Note that samples with one or two of the receptors staining positively have been omitted for clarity.

TABLE 4

Osteopontin expression in other samples.

| Diagnosis | OPN-a tumor | OPN-a adjacent normal | OPN-b tumor | OPN-b adjacent normal | OPN-c tumor | OPN-c adjacent normal |
|---|---|---|---|---|---|---|
| colorectal tumors | | | | | | |
| adenocarcinoma | n = 6<br>0-0.088<br>m = 0.024 | n = 4<br>0-0.543<br>m = 0.258 | n = 6<br>0-0.034<br>m = 0.009 | n = 4<br>0-0.069<br>m = 0.018 | n = 6<br>0-1.5<br>m = 0.474 | n = 4<br>0-1.020<br>m = 0.255 |
| colitis | | | | | | |
| diverticulitis | n = 1<br>m = 0.039 | na | n = 1<br>m = 0 | na | n = 1<br>m = 0 | na |
| ulcerative colitis | n = 3<br>0.059-0.166<br>m = 0.106 | na | n = 3<br>0-0.006<br>m = 0.002 | na | n = 3<br>0-0.045<br>m = 0.015 | na |

Example 6

Analysis of Subjects with Known Clinical Outcome

Clinical samples from subjects with breast cancer (such as DCIS) who have a known clinical outcome (for example, but not limited to, alive or dead after 1, 3, or 5 years; relapsed or relapse-free after 1, 3, or 5 years; suffering metastases or metastasis-free after a given time frame) are analyzed for the presence of OPN-c as described in Example 1. The skilled artisan will recognize that clinical outcomes can be defined in multiple ways.

The clinical samples will be staged and graded as described in Example 1. The presence of OPN-c will be detected using antibodies as described in Example 1 (e.g., staining scored using a typical 1+ to 3+ scale or a 0 to 300 scale). In some examples, the clinical samples are also analyzed for ER, PR, and HER2 expression as described in Example 1. The ability of OPN-c staining of the breast cancer samples to predict the outcome of the patient will be determined. It is expected that subjects having greater OPN-c expression (e.g., 3 on a 1+ to 3+ scale) will have a greater likelihood of adverse outcome (e.g., dead after 1, 3, or 5 years of diagnosis), as compared to subjects having less or no OPN-c expression (e.g., 0 or 1 on a 1+ to 3+ scale). Subjects having less OPN-c expression (e.g., 1 on a 1+ to 3+ scale) will have a greater likelihood of a favorable outcome (e.g., alive after 1, 3, or 5 years of diagnosis).

Example 7

Grading of Breast Cancer in Humans

This example describes particular methods that can be used to grade breast cancer, such as DCIS, in a human subject. However, one skilled in the art will appreciate that similar methods can be used, and that other cancer samples (e.g., from the colon or other tissue listed in Example 5) can be used in place of breast cancer samples. In some examples, such grading is performed before treating the subject.

Breast cancer cell or tissue samples are obtained from the subject. For example, a sample can be obtained from a tissue biopsy or needle aspirate using routine methods. In some examples, if a tissue biopsy sample is used, 1-100 μg of tissue can be obtained, for example using a fine needle aspirate. In particular examples, samples are used directly, or can be manipulated prior to use, for example, by fixing (e.g., using formalin) or embedding (e.g., in plastic or paraffin). In some examples, RNA or proteins are isolated from the tissue using routine methods (for example using a commercial kit).

In one example, OPN-c protein levels are determined in a breast cancer sample obtained from the subject. The breast cancer sample, such as a tissue or cell sample present on a substrate (such as a microscope slide) is incubated with an OPN-c antibody in an appropriate buffer for a time sufficient for the antibody to bind to OPN-c in the sample. The OPN-c/antibody complexes are detected, for example using microscopy. In some examples, the breast cancer sample (or other sample from the same subject) is analyzed for ER, PR, or HER2 protein levels using appropriate antibodies.

The antibody/protein complexes can be detected by a label on the antibody, or with a secondary labeled antibody. The resulting stained array slides can be scored by light microscopy by a pathologist according to the following criteria:

| Report Result | Staining Intensity Score | Microscope Observation |
|---|---|---|
| Positive: Any IHC staining of tumor cell membranes above background level whether it is complete or incomplete circumferential staining in more than 0% tumor cells | 3+<br><br><br><br><br>2.5 | Strong reactivity: Dark brown to black staining is usually, but not always, in a complete membrane pattern, producing a thick outline of the cell. Cytoplasmic reactivity may be absent or may be moderately intense when membrane staining is very intense. Submembranous cytoplasmic accentuation may be present.<br>Intense reactivity: Shades of brown staining of medium darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |

| Report Result | Staining Intensity Score | Microscope Observation |
|---|---|---|
| | 2+ | Moderate reactivity: Shades of brown staining of intermediate darkness (intensity). Membranous reactivity is usually but not always complete, producing a circular outline of the neoplastic cell. Incomplete membrane reactivity of moderate intensity is also considered 2+. The cytoplasmic reactivity is of weaker intensity than the membrane reactivity. |
| | 1.5 | Slight reactivity: Staining of intermediate intensity that is membraneous. Cytoplasmic reactivity that is uniform and involves all the cytoplasm may be present, but should not be evaluated for positivity. |
| | 1+ | Weak reactivity: Faint or light brown reactivity that is membranous. Cytoplasmic reactivity that is uniform and involves all the cytoplasm may be present, but should not be evaluated for positivity. |
| Negative: Absence of membrane staining above background in all tumor cells. Presence of cytoplasmic in the absence of membrane staining. | 0.5 | Trace reactivity: Trace brown reactivity where membranous and cytoplasmic localization is indeterminate. |
| | 0 | No reactivity |

The resulting score can be used to grade, stage, or prognose the tumor (e.g., see Table 1).

In other examples, the relative amount of OPN-c (or ER, PR, HER2)/antibody complexes in the breast cancer sample from the subject can be compared to a reference value, such as a relative amount of OPN-c (or ER, PR, HER2)/antibody complexes present in a normal breast sample or a breast cancer sample from a subject having a known grade of tumor (e.g., grade 1, 2 or 3). The presence of significantly greater OPN-c/antibody complexes in the test breast cancer sample relative to the control indicates that the subject has a higher grade or stage cancer (e.g., grade 3) and a worse prognosis, while the presence of less OPN-c/antibody complexes indicates that the subject has a lower grade or stage cancer (e.g., grade 1) and a better prognosis.

In one example, OPN-c mRNA expression levels are determined in a breast cancer sample obtained from the subject. cDNA is generated from the RNA isolated from the breast cancer sample (for example using a commercial reverse transcription kit). OPN-c cDNA is amplified using appropriate primers (for example using primers having a detectable label), and the resulting OPN-c amplicons detected. The relative amount of OPN-c amplicons in the breast cancer sample can be normalized (e.g., to a housekeeping gene) and compared to a reference value, such as a relative amount of OPN-c amplicons present in a normal breast sample or a breast cancer sample from a subject having a known grade or stage of tumor (e.g., grade 1, 2 or 3). The presence of higher amounts of OPN-c amplicons in the test breast cancer sample indicates that the subject has a higher grade or stage cancer (e.g., grade 3) and a worse prognosis, while the presence of less OPN-c amplicons indicates that the subject has a lower grade or stage cancer (e.g., grade 1) and a better prognosis.

REFERENCES

1. Chan and Sell. Tumor markers. In: Burtis C A Ashwood E R, editors. Tietz fundamental of clinical chemistry, 5th ed. Philadelphia: W B Saunders; 2001. p. 390-413.
2. Henry N L, Hayes D F. Uses and abuses of tumor markers in the diagnosis, monitoring, and treatment of primary and metastatic breast cancer. Oncologist 2006; 11:541-552.
3. Clark G M. In: Harris J L M, Morrow M, Hellman S, editors. Diseases of the Breast. Philadelphia: Lippincott-Raven; 1996. p. 461-485.
4. Andre F, Pusztai L. Molecular classification of breast cancer: implications for selection of adjuvant chemotherapy. Nat Clin Pract Oncol 2006; 3:621-632.
5. Kleer et al., EZH2 is a marker of aggressive breast cancer and promotes neoplastic transformation of breast epithelial cells. Proc Natl Acad Sci USA 2003; 100:11606-11611.
6. Desruisseau et al., Clinical relevance of amphiregulin and VEGF in primary breast cancers. Int J Cancer 2004; 111:733-740.
7. Zhang et al., Growth factor signaling induces metastasis genes in transformed cells: molecular connection between Akt kinase and osteopontin in breast cancer. Mol Cell Biol 2003; 23:6507-6519.
8. Rudland et al., Prognostic significance of the metastasis-associated protein osteopontin in human breast cancer. Cancer Res 2002; 62:3417-3427.
9. Singhal et al., Elevated plasma osteopontin in metastatic breast cancer associated with increased tumor burden and decreased survival. Clin Cancer Res 1997; 3:605-611.
10. Weber G F, Ashkar S. Stress response genes—the genes that make cancer metastasize. J Mol Med 2000; 78:404-408.
11. Kon et al., Antibodies to different peptides in osteopontin reveal complexities in the various secreted forms. J Cell Biochem 2000; 77:487-498.
12. Crawford et al., Distinct roles of osteopontin in host defense activity and tumor survival during squamous cell carcinoma progression in vivo. Cancer Res 1998; 58:5206-5215.
13. Kasugai et al., Differential regulation of the 55 and 44 kDa forms of secreted phosphoprotein 1 (SPP-1, osteopontin) in normal and transformed rat bone cells by osteotropic hormones, growth factors and a tumor promoter. Bone Miner 1991; 13:235-250.
14. He B, Mirza M, Weber G F. An osteopontin splice variant induces anchorage independence in human breast cancer. Oncogene 2006; 25:2192-2202.
15. Elston C W, Ellis I O. Pathological prognostic factors in breast cancer. I. The value of histological grade in breast cancer: experience from a large study with long-term follow-up. Histopathol 1991; 19:403-410.
16. Lehmann E L, D'Abrera H J M. Nonparametrics: Statistical Methods Based on Ranks Prentice-Hall: Englewood Cliffs; 1998.

17. Bartfay et al., Comparing the predictive value of neural network models to logistic regression models on the risk of death for small-cell lung cancer patients. Eur J Cancer Care 2006; 15:115-124.
18. Bassi et al., Prognostic accuracy of an artificial neural network in patients undergoing radical cystectomy for bladder cancer: a comparison with logistic regression analysis. BJU Int 2007; 99:1007-1012.
19. Rakha et al., Prognostic markers in triple-negative breast cancer. Cancer 2007; 109:25-32.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A method of treating a patient having a triple negative breast cancer tumor, the method comprising:
   (I) grading the triple negative breast cancer tumor in the patient by:
      (1) obtaining a sample of the triple negative breast cancer tumor from the patient;
      (2) contacting the sample of the triple negative breast cancer tumor with an antibody that specifically binds to the splice junction of the OPN-c protein under conditions suitable to form a complex of the OPN-c protein and the antibody, wherein the antibody is anti-human OPN-c IgY;
      (3) detecting the expression intensity level of the OPN-c protein in the sample contacted with the antibody in (I)(2) via immunohistochemical staining; and
      (4) quantifying the expression intensity level of the OPN-c protein detected in the sample in (I)(3); and
      (5) grading the tumor on the basis of OPN-c expression intensity level; and
   (II) treating the patient with:
      (1) an aggressive therapeutic protocol when the triple negative breast cancer tumor has a grade of 2 or 3 on the basis of OPN-C protein expression level, wherein the aggressive therapeutic protocol comprises mastectomy or lumpectomy combined with radiotherapy and/or chemotherapy; and
      (2) a less aggressive therapeutic protocol when the triple negative breast cancer tumor has a grade of 1 on the basis of OPN-C protein expression level, wherein the less aggressive therapeutic protocol consists of lumpectomy.

2. A method for treating a breast cancer patient suspected of having a triple negative breast cancer, the method comprising:
   (I) assessing triple negative breast cancer in the patient by:
      (1) obtaining a breast cancer tumor sample from the patient; and
      (2) detecting an expression level of estrogen receptor (ER), progesterone receptor (PR), and human epidermal growth factor receptor 2 (HER2) in the tumor sample, wherein the expression level of estrogen receptor (ER), progesterone receptor (PR), and human epidermal growth factor receptor 2 (HER2) is indicative of triple negative breast cancer;
(II) grading the tumor sample when triple negative breast cancer is indicated in (I)(2) by:
  (1) contacting the tumor sample with an antibody that specifically binds to the splice junction of the OPN-c protein under conditions suitable to form a complex of the OPN-c protein and the antibody, wherein the antibody is anti-human OPN-c IgY;
  (2) detecting the expression intensity level of the OPN-c protein in the tumor sample contacted with the antibody in (II)(1) via immunohistochemical staining; and
  (3) quantifying the expression intensity level of the OPN-c protein detected in the tumor sample in (II)(2); and
  (4) grading the triple negative breast cancer on the basis of OPN-c expression intensity level; and
(III) treating the patient with:
  (1) an aggressive therapeutic protocol when the triple negative breast cancer tumor has a grade of 2 or 3 on the basis of OPN-C protein expression level, wherein the aggressive therapeutic protocol comprises mastectomy, or comprises lumpectomy combined with radiotherapy and/or chemotherapy; or
  (2) a less aggressive therapeutic protocol when the triple negative breast cancer tumor has a grade of 1 on the basis of OPN-C protein expression level, wherein the less aggressive therapeutic protocol consists of lumpectomy.

3. The method of claim 1 or 2, wherein the triple negative breast cancer is ductal carcinoma in situ (DCIS).

4. The method of claim 1, wherein the triple negative breast cancer tumor has no detectable level of estrogen receptor (ER), progesterone receptor (PR), and human epidermal growth factor receptor 2 (HER2).

5. The method of claim 1, wherein the expression level of the OPN-c protein detected in the sample in (I)(3) is quantified with a staining intensity score.

6. The method of claim 1, wherein:
  the expression level of the OPN-c protein detected in the sample in (I)(3) is quantified with a staining intensity score;
  a staining intensity score of 0-1.5 is indicative of a grade 0-1 tumor;
    a staining intensity score of 2-2.5 is indicative of a grade 2 tumor; and
    a staining intensity score of 3 or more is indicative of a grade 3 tumor.

7. The method of claim 2, wherein the expression level of the OPN-c protein detected in the sample in (II)(2) is quantified with a staining intensity score.

8. The method of claim 2, wherein:
  the expression level of the OPN-c protein detected in the sample in (II)(2) is quantified with a staining intensity score;
  a staining intensity score of 0-1.5 is indicative of a grade 0-1 tumor;
  a staining intensity score of 2-2.5 is indicative of a grade 2 tumor; and
  a staining intensity score of 3 or more is indicative of a grade 3 tumor.

9. The method of claim 1, wherein the tumor grade is made on the basis of OPNc expression without consideration of OPNa or OPNb expression.

10. The method of claim 2, wherein the tumor grade is made on the basis of OPNc expression without consideration of OPNa or OPNb expression.

* * * * *

```
                            SEQUENCE LISTING

<160> NUMBER OF SEQ ID NOS: 16

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide primer for OPN-a

<400> SEQUENCE: 1
atctcctagc cccacagaat                                                   20

<210> SEQ ID NO 2
<211> LENGTH: 22
<212> TYPE: DNA
<213> ORGANISM: Artificial sequence
<220> FEATURE:
<223> OTHER INFORMATION: Synthetic oligonucleotide primer for OPN-a

<400> SEQUENCE: 2
catcagactg gtgagaatca tc                                                22

<210> SEQ ID NO 3
<211> LENGTH: 19
<212> TYPE: DNA
<213> ORGANISM: Artificial sequence
<220> FEATURE:
<223> OTHER INFORMATION: Synthetic oligonucleotide primer for OPN-b

<400> SEQUENCE: 3
atctcctagc cccagagac                                                    19

<210> SEQ ID NO 4
<211> LENGTH: 23
<212> TYPE: DNA
<213> ORGANISM: Artificial sequence
<220> FEATURE:
<223> OTHER INFORMATION: Synthetic oligonucleotide primer for OPN-b

<400> SEQUENCE: 4
aaaatcagtg accagttcat cag                                               23

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide primer for OPN-c

<400> SEQUENCE: 5
tgaggaaaag cagaatgctg                                                   20

<210> SEQ ID NO 6
<211> LENGTH: 20
<212> TYPE: DNA
```

```
<213> ORGANISM: Artificial sequence
<220> FEATURE:
<223> OTHER INFORMATION: Synthetic oligonucleotide primer for OPN-c

<400> SEQUENCE: 6
gtcaatggag tcctggctgt                                                     20

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide primer for beta-Actin

<400> SEQUENCE: 7
ggcggcacca ccatgtaccc t                                                   21

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide primer for beta-Actin

<400> SEQUENCE: 8
aggggccgga ctcgtcatac t                                                   21

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide primer for Ck-19

<400> SEQUENCE: 9
cccgcgacta cagccacta                                                      19

<210> SEQ ID NO 10
<211> LENGTH: 19
<212> TYPE: DNA
<213> ORGANISM: Artificial sequence
<220> FEATURE:
<223> OTHER INFORMATION: Synthetic oligonucleotide primer for Ck-19

<400> SEQUENCE: 10
ctcatgcgca gagcctgtt                                                      19

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide primer for aP2

<400> SEQUENCE: 11
tcagtgtgaa tggggatgtg                                                     20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide primer for aP2

<400> SEQUENCE: 12
gtggaagtga cgcctttcat                                                     20
```

```
<210> SEQ ID NO 13
<211> LENGTH: 26
<212> TYPE: DNA
<213> ORGANISM: Artificial sequence
<220> FEATURE:
<223> OTHER INFORMATION: Synthetic oligonucleotide primer for GAPDH

<400> SEQUENCE: 13
tgaaggtcgg agtcaacgga tttggt                                          26

<210> SEQ ID NO 14
<211> LENGTH: 24
<212> TYPE: DNA
<213> ORGANISM: Artificial sequence
<220> FEATURE:
<223> OTHER INFORMATION: Synthetic oligonucleotide primer for GAPDH

<400> SEQUENCE: 14
catgtgggcc atgaggtcca ccac                                            24

<210> SEQ ID NO 15
<211> LENGTH: 22
<212> TYPE: DNA
<213> ORGANISM: Artificial sequence
<220> FEATURE:
<223> OTHER INFORMATION: Synthetic oligonucleotide primer for
      osteopontin

<400> SEQUENCE: 15
caaacgccga ccaagggaaa ac                                              22

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide primer for
      osteopontin

<400> SEQUENCE: 16
cttctttctc agtttattgg t                                               21
```